US005730757A

United States Patent [19]
Benetti et al.

[11] Patent Number: 5,730,757
[45] Date of Patent: Mar. 24, 1998

[54] ACCESS PLATFORM FOR INTERNAL MAMMARY DISSECTION

[75] Inventors: Federico J. Benetti, Santa Fe, Argentina; Charles S. Taylor, San Francisco, Calif.; William N. Aldrich, Redwood City, Calif.; Ivan Sepetka, Los Altos, Calif.; Robert G. Matheny, Carmel, Ind.; Eugene E. Reis, San Jose, Calif.; Brent Regan, Davis, Calif.; Richard M. Ferrari, Saratoga, Calif.

[73] Assignee: Cardiothoracic Systems, Inc., Cupertino, Calif.

[21] Appl. No.: 604,161

[22] Filed: Feb. 20, 1996

[51] Int. Cl.⁶ .................................................... A61B 17/02
[52] U.S. Cl. .......................... 606/198; 600/201; 600/214
[58] Field of Search .................................. 600/201–234; 606/191, 198

[56] References Cited

U.S. PATENT DOCUMENTS

| | | |
|---|---|---|
| Re. 34,150 | 12/1992 | Santilli et al. |
| 4,049,000 | 9/1977 | Williams . |
| 4,434,791 | 3/1984 | Darnell . |
| 4,627,421 | 12/1986 | Symbas et al. |
| 4,702,230 | 10/1987 | Pelta . |
| 4,726,356 | 2/1988 | Santilli et al. |
| 4,747,395 | 5/1988 | Brief . |
| 4,829,985 | 5/1989 | Couetil . |
| 4,852,552 | 8/1989 | Chaux . |
| 4,865,019 | 9/1989 | Phillips . |
| 4,884,559 | 12/1989 | Collins . |
| 4,971,037 | 11/1990 | Pelta . |
| 4,993,862 | 2/1991 | Pelta . |
| 5,052,373 | 10/1991 | Michelson . |
| 5,167,223 | 12/1992 | Koros et al. .............. 128/20 |

FOREIGN PATENT DOCUMENTS

| | | |
|---|---|---|
| 168216 | 9/1921 | United Kingdom . |
| 2 267 827 | 12/1993 | United Kingdom . |

OTHER PUBLICATIONS

Campalani, G., M.D., et al., A new self–retaining internal mammary artery retractor, J. Cardiovas. Surg. 28, 1987.

Pittman, John, M.D., et al., Improved Visualization of the Internal Mammary Artery With a New Retractor System, Ann. Thorac. Surg. (1989;48:869–70).

Angelini, G. D., M.D., et al., A Fiber–Optic Retractor for Harvesting the Internal Mammary Artery, Ann. Thorac. Surg. (1990;50:314–5).

Phillips, Steven J., M.D., et al., A versatile retractor for use in harvesting the internal mammary artery and performing standard cardiac operations, J. Thorac. Cardiovasc. Surg. (1989;97:633–5).

Itoh, Toshiaki, M.D., et al., New Modification of a Mammary Artery Retractor, Ann. Thorac. Surg. (1994;57:1670–1).

Roux, D., M.D., et al., Internal mammary artery dissection: A three dimensional sternal retractor, J. Cardiovasc. Surg. (1989;30:996–7).

USSC Cardiovascular Thora–Lift™, United States Surgical Corporation, Norwalk, Connecticut, Product Brochure.

(List continued on next page.)

*Primary Examiner*—Gary Jackson
*Assistant Examiner*—William Lewis
*Attorney, Agent, or Firm*—Lyon & Lyon LLP

[57] ABSTRACT

An access platform having a first and a second blade interconnected to a spreader member that laterally drives the blades apart or together and support pads interconnected to the first blade. A torsional member is operably interconnected to the first blade and the spreader member and is used to vertically displace the first blade in either direction and, thus, increase a surgeon's working space and visual access for the dissection of an internal mammary artery. A tissue retractor interconnected to the blades is used to draw the soft tissue around an incision away from the surgeon's working area.

45 Claims, 20 Drawing Sheets

OTHER PUBLICATIONS

Pilling Surgical Instruments, A Rusch International Company, Brochure.

Delacroix–Chevalier Surgical Instruments, IMA Savings Packages Brochure.

Ancalmo, N., and J.L. Ochsner: A Modified Sternal Retractor, Ann. Thorac. Surg. 21 (1976) 174.

Beg, R.A., H. Naraghipour, E.B. Kay, and P. Rullo: Internal Mammary Retractor, Ann. Thorac. Surg. 39 (1985) 286–287.

Chaux, A., and C. Blanche: A New Concept in Sternal Retraction: Applications for Internal Mammary Artery Dissection and Valve Replacement, Ann. Thorac. Surg. 42 (1986) 473–474.

McKeown, P.P., J. Crew, E.S. Hanna, and R. Jones: A Modified Sternal Retractor for Exposure of the Internal Mammary Artery, Ann. Thorac. Surg. 32 (1981) 619.

Vincent, J.G.: A Compact Single Post Internal Mammary Artery Dissection Retractor, Eur. J. Cardio–Thor. Surg. 3 (1989) 276–277.

ACCESS PLATFORM FOR INTERNAL MAMMARY DISSECTION

FIELD OF THE INVENTION

This invention relates to retractors, and more particularly to an access platform that facilitates access to the interior of the chest cavity during surgical procedures.

BACKGROUND OF THE INVENTION

Diseases of the cardiovascular system affect millions of people each year and are a leading cause of death in the United States and throughout the world. The cost to society from such diseases is enormous both in terms of lives lost and the cost of treating cardiac disease patients through surgery. A particularly prevalent form of cardiovascular disease is a reduction in the blood supply to the heart caused by atherosclerosis or other conditions that create a restriction is blood flow at a critical point in the cardiovascular system leading to the heart. In many cases, a blockage or restriction in the blood flow leading to the heart can be treated by a surgical procedure known as a Coronary Artery bypass Graft (CABG) procedure, which is more commonly known as a "heart bypass" operation. In the CABG procedure, the surgeon either removes a portion of a vein from another part of the body to use as a graft and installs the graft at points that bypass the obstruction to restore normal blood flow to the heart or detaches one end of an artery and connects that end past the obstruction while leaving the other end attached to the arterial supply to restore normal blood flow to the heart.

Although the CABG procedure has become relatively common, i.e., heart bypass surgery is performed in one of every thousand persons in the United States, the procedure is lengthy and traumatic and can damage the heart, the central nervous system, and the blood supply. In a conventional CABG procedure, the surgeon cuts off the blood flow to the heart and then stops the heart from beating in order to install the graft. Thus, in order to perform the conventional CABG procedure, the surgeon must make a long incision down the middle of the chest, saw through the entire length of the sternum, spread the two halves of the sternum apart, and then perform several procedures necessary to attach the patient to a cardiopulmonary bypass machine to continue the circulation of oxygenated blood to the rest of the body while the graft is sewn in place.

The CABG procedure further requires that a connection for the flow of blood be established between two points that "by pass" a diseased area and restore an adequate blood flow. Typically, one end of a graft is sewn to the aorta, while the other end of the graft is sewn to a coronary artery, such as the left anterior descending (LAD) artery that provides blood flow to the main muscles of the heart. This procedure is known as a "free bypass graft." Alternatively, the IMA pedicle is dissected off of the chest wall, while still attached to its arterial supply, and attached to the LAD past the obstruction. This procedure is known as an "in situ bypass graft."

In an in situ bypass graft, the IMA must be dissected from its connective tissue until there is sufficient slack in the IMA to insure that the graft does not kink after it is installed. The IMAs, left and right, extend from the subclavian arteries in the neck to the diaphragm and run along the backside of the rib cage adjacent the sternum. During a conventional in situ bypass graft, typically the left half of the sternum is raised to increase the surgeon's access to the left IMA (LIMA) and the heart. A device used for this type of sternal retraction is disclosed in United Kingdom Patent Application No. GB 2267827 A, "A device for Internal Mammary artery dissection."

Although several efforts have been made to make the CABG procedure less invasive and less traumatic, most techniques still require cardiac bypass and cardioplegia (stoppage of the heart). The safety and efficacy of CABG procedure could be improved if the surgeon could avoid the need to stop the heart from beating during the procedure, thereby eliminating the need to connect the patient to a cardiopulmonary bypass machine to sustain the patient's life during the CABG procedure and, thus, eliminate the need for the lengthy and traumatic surgical procedures necessary to connect the patient to a cardiopulmonary bypass machine. In recent years, a small number of surgeons have begun performing CABG procedures using surgical techniques especially developed to enable surgeons to perform the CABG procedure while the heart is still beating. In such procedures, there is no need for any form of cardiopulmonary bypass, no need to perform the extensive surgical procedures necessary to connect the patient to a cardiopulmonary bypass machine, cardioplegia is rendered unnecessary, the surgery is much less invasive and traumatic, and the entire procedure can typically be achieved through one or two comparatively small incisions (thoracotomies) in the chest.

Despite these advantages, the beating-heart CABG procedure is not widely practiced, in part, because of the difficulty in performing the necessary surgical procedures with conventional instruments while the heart is still beating. If specially designed instruments were available so that the CABG procedure could more easily be performed on the beating heart, the beating-heart CABG procedure would be more widely practiced and the treatment of cardiovascular disease would be improved in a significant part of the cardiovascular disease patient population.

Since the "beating-heart" CABG procedure is performed while the heart muscle is continuing to beat or contract, an anastomosis is difficult to perform because the blood continues to flow and the heart continues to move while the surgeon is attempting to sew the graft in place. The surgical procedure necessary to install the graft requires placing a series of sutures through several extremely small vessels that continue to move during the procedure. The sutures must become fully placed so that the graft is firmly in place and does not leak. It is also important that the procedure be performed rapidly because the blood flow through the artery may be interrupted or reduced during the procedure to allow the graft to be installed. This can cause ischemia, which should be minimized. Also, the surgeon's working space and visual access are limited because the surgeon may be working through a small incision in the chest or may be viewing the procedure on a video monitor, such that the site of the surgery is viewed via a surgical scope.

The "beating-heart" CABG procedure could be greatly improved if the surgeon's working space and visual access to the heart and the IMA were increased and improved. Current methods to increase and improve the surgeon's working space and visual access include laterally spreading or retracting the ribs with a conventional rib spreader/retractor, and then vertically displacing one of the retracted ribs relative to the other retracted rib to create a "tunnel" under the rib cage. To vertically displace one of the retracted ribs, some force external to the rib spreader must be applied to the rib. Typically, a surgeon's assistant will push or pull upwardly on the rib with a device having a rib blade inserted under the rib. However, the surgeon's assistant must then hold the rib in a vertically displaced position for the duration of the IMA dissection, resulting in an undesirable addition of another set of hands around the surgical area.

Another method used by surgeons to vertically displace the retracted rib is to insert a rib blade under the retracted rib and then attach the rib blade to a winch located above the patient. The winch is then operated to pull upwardly on the rib and hold it in a vertically displaced position. However, it is not at all uncommon for the patient to be raised off the operating table by the winch. This is undesirable because if the rib begins to crack or break, the weight of the patient's body will cause the rib to continue to break until the patient reaches the operating table.

While using these methods to vertically displace one of the retracted ribs, it may be desirable to further increase a surgeon's working space and visual access by depressing the sternum or the other retracted rib. However, depression of the sternum or the other retracted rib undesirably adds further sets of hands around the surgical site.

Furthermore, these methods and devices tend to limit where the thoracotomy can be performed. For example, if the thoracotomy is performed on the lateral side of the chest, the conventional rib spreader would tend to "stand-up" vertically from the ribs it is retracting such that it would intrude on the surgeon's working space. In addition, if a winch is used to offset the ribs, the lifting action of the winch will tend to rotate the patient to an undesirable and often unstable position for performing the IMA.

Equally important to improving the "beating heart" CABG procedure, is the ability to retract the soft tissue around the incision in the chest to draw the soft tissue away from the surgeon's working area. However, none of the methods or devices described above provide the ability to perform soft tissue retraction.

Thus, in view of the shortcomings of these devices and methods for increasing a surgeon's working space and visual access during a "beating-heart" CABG procedure, it would be desirable to have a device that is capable of laterally spreading the ribs and vertically displacing opposing retracted ribs relative to each other, that is capable of depressing the sternum, that is self-contained such that the force necessary to spread and vertically displace the ribs, and the force necessary to depress the sternum, is applied by the access platform itself rather than through additional external devices, that does not limit the location where a thoracotomy can be performed, and that is capable of soft tissue retraction.

SUMMARY OF THE INVENTION

The access platform of the present invention serves to facilitate the dissection of an internal mammary artery (IMA), including both proximal and distal dissection, and access to the heart during a "beating heart" Coronary Artery Bypass Graft (CABG) procedure by increasing the surgeon's working space and visual access. The access platform of the present invention is preferably capable of laterally spreading the ribs, vertically displacing the opposingly retracted ribs relative to each other and depressing the sternum to cause a "tunnel" effect under the retracted ribs. Moreover, it is preferably self-contained such that the force necessary to spread and vertically displace the ribs is applied by the access platform itself rather than through additional external devices. The access platform preferably comprises a first and a second blade interconnected to a spreader member that laterally drives the blades apart or together, support pads interconnected to the blades, and a bi-directional torsional member interconnected to a blade and the spreader member. The torsional member causes the interconnected blade to be vertically displaced in either direction and, thus, increases the surgeon's working space and visual access to the IMA.

In addition, the access platform preferably includes an integrated tissue retractor, a hinged connector interconnected to the blades and the spreader member, and a port interconnected to the blades. The tissue retractor advantageously draws the soft tissue around an incision away from the surgeon's working area. The port advantageously provides a mount for a heart stabilizer, a scope for IMA take down, an IMA clamp, an IMA holder or other tools necessary for a "beating heart" CABG procedure. The hinged connector advantageously pivots the access platform away from the surgeon's working area.

It is an object of the present invention to provide an improved access platform.

Another object of the present invention is to provide an improved tissue retractor.

Further objects and advantages of the present invention will become apparent from a consideration of the drawings and the ensuing description.

DESCRIPTION OF THE PREFERRED EMBODIMENT

Figure 1:
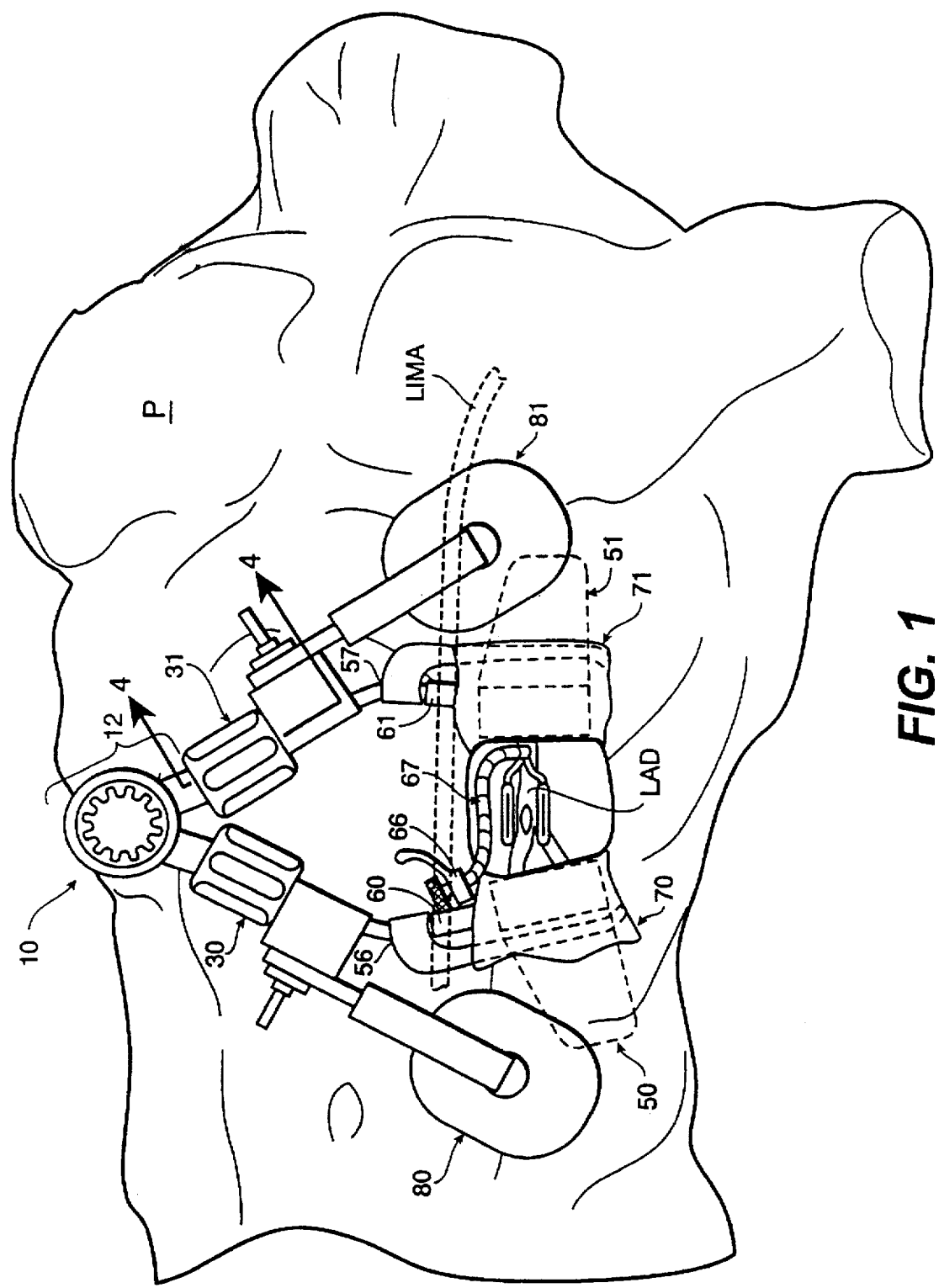
FIG. 1 is a top view of an embodiment of an access platform of the present invention disposed over the chest of a patient.

Referring now in detail to the drawings, therein illustrated is a novel access platform that facilitates the dissection of an internal mammary artery (IMA), including both proximal and distal dissection, and access to the heart during a "beating heart" Coronary Artery Bypass Graph (CABG) procedure by increasing the surgeon's working space and visual access. Turning to FIG. 1, the access platform 10 incorporating a preferred embodiment of the present invention, is shown disposed over the outline of a patient's chest P. An incision in the patient's chest P adjacent to the LIMA (shown in phantom) exposes an LAD artery on the exterior of the patient's heart. Preferably, the access platform 10 comprises a pair of blades 50 and 51, a pair of support pads 80 and 81, a pair of tissue retractors 70 and 71, a pair of torsional members 30 and 31, and a spreader member 12. The torsional members 30 and 31 and the spreader member 12 preferably extend away from the blades 50 and 51 and the tissue retractors 70 and 71 and, thus, the chest incision, in a plane relatively parallel to the patient's chest. As a result, the access platform 10 advantageously maintains a low profile that remains substantially clear of the surgeon's working space.

Figure 2:
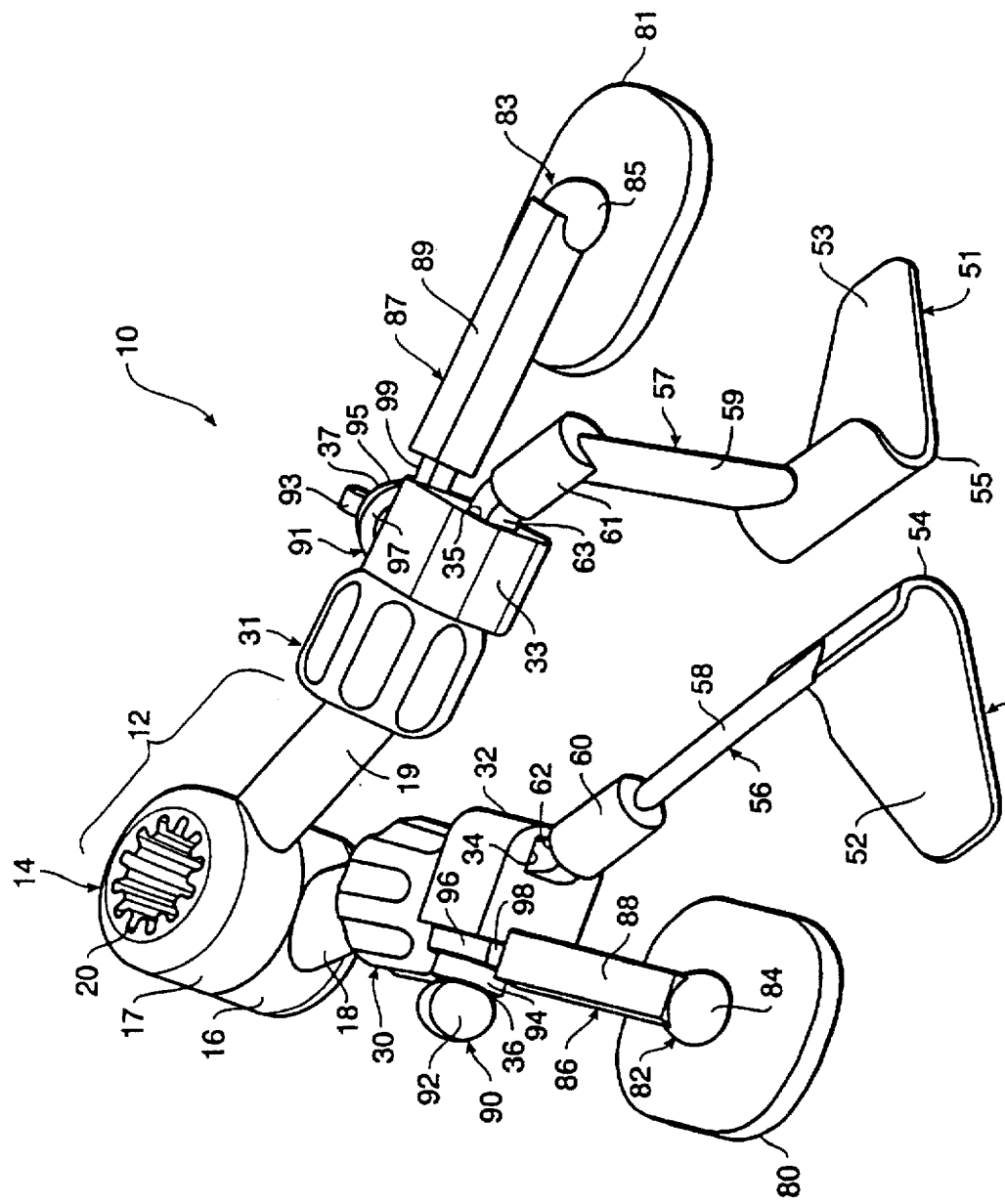
FIG. 2 is an isometric view of the access platform shown in FIG. 1 less the tissue retractor elements.

Referring to FIG. 2, the components of the access platform 10 are shown less the tissue retractors 70 and 71. The spreader member 12 preferably comprises a rotatable hub 14 including operably coupled upper and lower hub halves 17 and 16. A pair of spreader arms 19 and 18 extend from the upper and lower hubs 17 and 16, respectively, and connect to the torsional members 31 and 30, respectively. Preferably, the hub 14 includes a harmonic gear drive 20 used to rotate the upper hub half 17 relative to the lower hub half 16 and, thus, spread or close the spreader arms 18 and 19 to retract or relax the patient's ribs.

Figure 3:
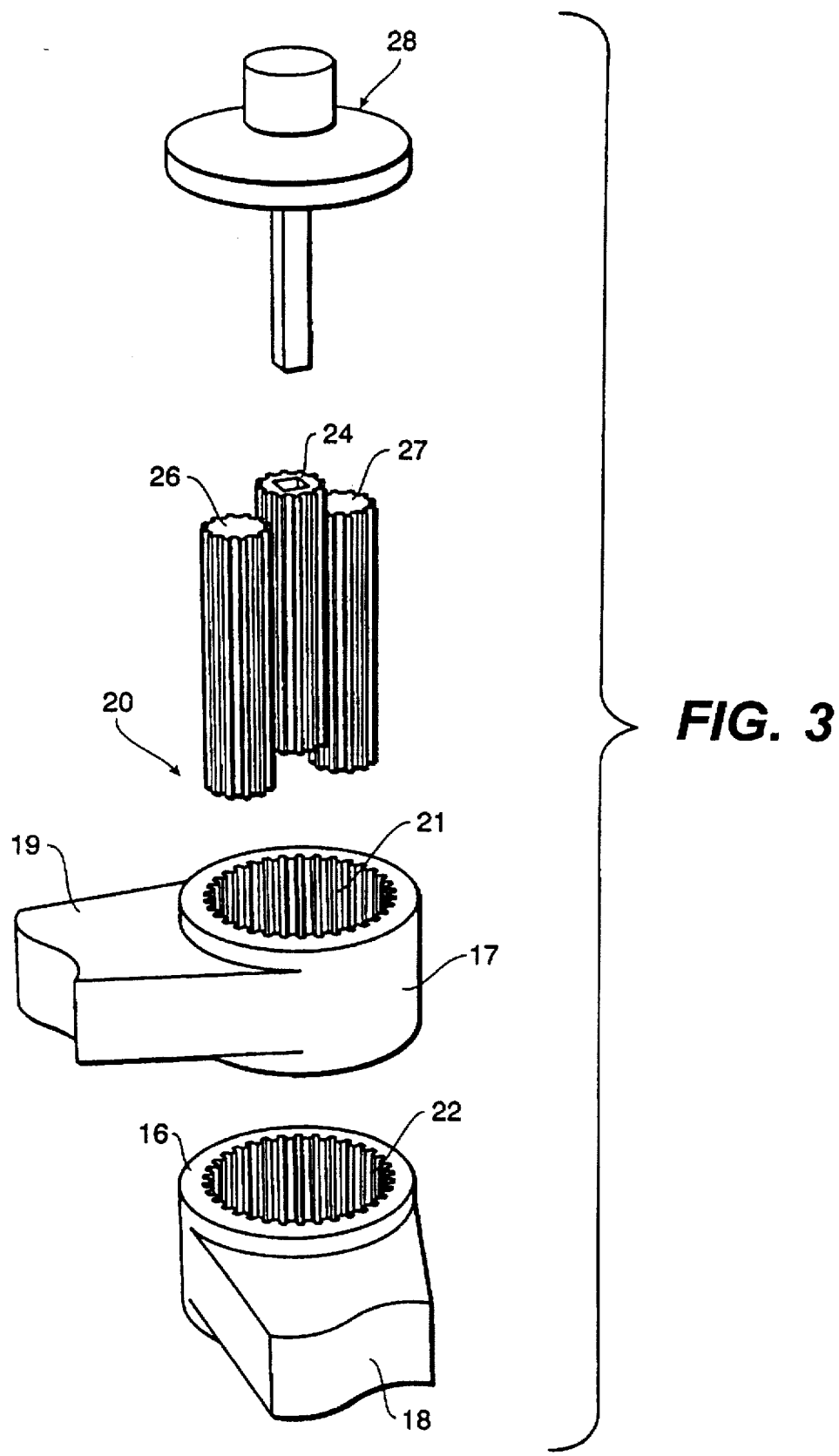
FIG. 3 is an exploded isometric view of a harmonic gear drive in the hub element of the access platform in FIG. 1.

Turning to FIG. 3, the harmonic gear drive 20 comprises ring gears 21 and 22, a pinion 24, idler gears 26 and 27, and a drive hub 28. The ring gears 21 and 22 are formed on the inner walls of the upper and lower hub halves 17 and 16, respectively. The idler gears 26 and 27 are operably connected to the pinion 24 and ring gears 21 and 22. Preferably, the effective gear ratios between the ring gears 21 and 22 are in the range of about 20–40:1, and the gear ratio between the pinion 24 and the ring gears 21 and 22 are in the range of about 3–5:1. Thus, only a relatively low torque is needed to turn the drive hub 28, which is connected to the pinion 24, to drive the ring gears 21 and 22 at a relatively high torque to rotate the upper hub 17 relative to the lower hub 16 and spread a patient's ribs apart.

Alternatives to the harmonic gear drive 20 include the use of a ratchet mechanism, a wrap spring mechanism or a lock nut mechanism (not shown) with the hub 14. Thus, a wrench or special tool can be attached to the upper hub half 17 to rotate it relative to the lower hub half 16 while the operator holds onto the spreader arm 18 or the lower hub half 16 with another wrench or special tool. Once the upper hub half 17 is rotated to a desired position relative to the lower hub 16, the ratchet or wrap spring mechanism prevents reverse rotation of the upper hub half 17. If a lock nut mechanism is used, a lock nut is simply tightened to prevent reverse rotation after the upper hub half 17 is rotated relative to the lower hub 16 to a desired position.

Referring to FIG. 2, the blades 50 and 51 preferably include elongated vanes 52 and 53, which slide beneath a plurality of the patient's ribs, and recessed arcuate throats 54 and 55 that receive the patient's retracted ribs that are proximal to the chest incision. The benefits of the recessed throats 54 and 55 and the elongated vanes 52 and 53 will be discussed below with regard to the operation of the access platform 10.

Blade arms 56 and 57 interconnect the blades 50 and 51 to the rest of the access platform 10. The blade arms 56 and 57 comprise arm stems 62 and 63 received in sockets 34 and 35 in torque bases 32 and 33. The sockets 34 and 35 and the stems 62 and 63 are constructed such that the blade arms 56 and 57 are releasably connected to the torque bases 32 and 33. The stems 62 and 63, which extend relatively horizontally from the torque bases 32 and 33, include pivot sections 60 and 61 extending therefrom. Branches 58 and 59 extend outwardly and downwardly away from the pivot sections 60 and 61 and are attached to the throats 54 and 55 of the blades 50 and 51. This blade arm construction advantageously directs the bulk of the access platform 10 away from the surgeon's working area.

The support pads 80 and 81 are connected to adjustable arms 86 and 87 by swivel connectors 82 and 83 that are preferably constructed as ball and socket type connectors. The adjustable arms 86 and 87 preferably include external shafts 88 and 89 slidably received over and operably connected to internal shafts 98 and 99. The external shafts 88 and 89 are preferably operably connected to the internal shafts 98 and 99 via a ratchet lever mechanism (not shown). The internal shafts 98 and 99 of the adjustable arms 86 and 87 are further connected to lock positioners 90 and 91. The lock positioners 90 and 91, which are attached to the torque bases 32 and 33, comprise a ratchet or a wrap spring type mechanism (not shown) or, alternatively, comprise opposing face gears 94 and 96, 95 and 97. Tabs 92 and 93 rotate and cooperate with cammed or serrated surfaces 36 and 37 on the outer face of the outer face gears 94 and 95 to engage and disengage the opposing face gears 96 and 97. Thus, when the tabs 92 and 93 are rotated to disengage the face gears 94 and 96, 95 and 97, the support pads 80 and 81 can be rotated to a desired position. Once the support pads 80 and 81 are in position, the tabs 92 and 93 are rotated to engage the face gears 94 and 96, 95 and 97 and, thus, lock the support pads 80 and 81 in place.

The torsional members 30 and 31 are operably connected to the torque bases 32 and 33 and the spreader arms 18 and 19 to enable the access platform 10 to both laterally retract and vertically displace a patient's ribs R. Thus, the torsional members 30 and 31 enable the access platform 10 to be advantageously self-contained such that the force necessary to spread and vertically displace a patient's ribs, and the force necessary to depress the patient's sternum, is applied by the access platform 10 itself rather than through additional external devices.

Figure 4:
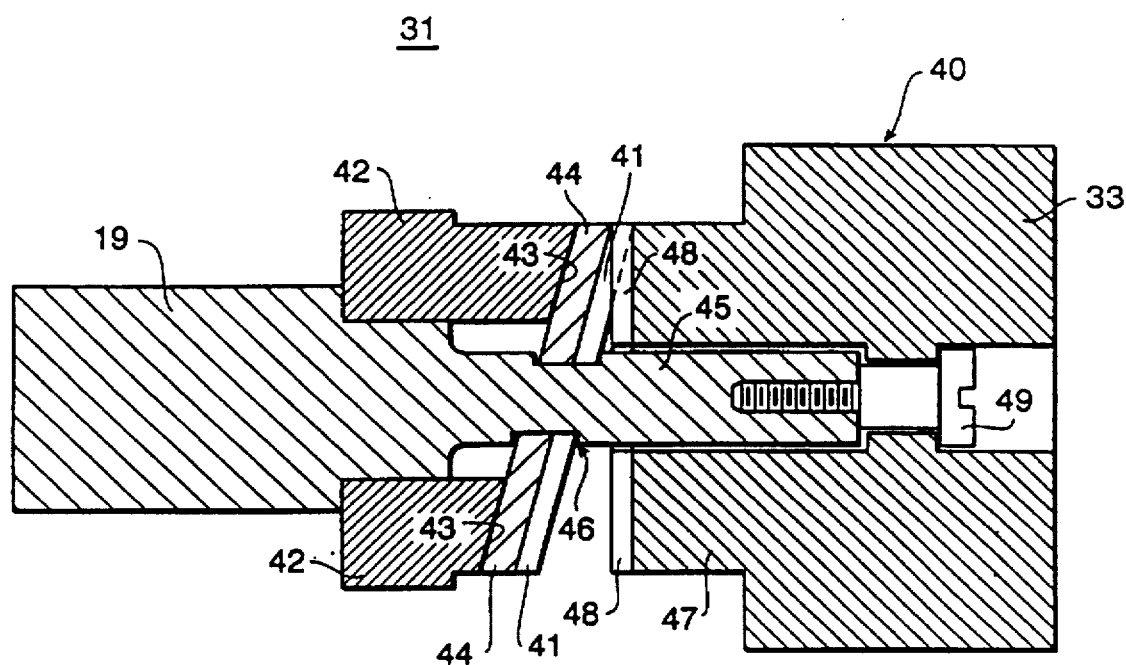
FIG. 4 is a cross-sectional view of a reduction gear assembly in the torsional member element of the access platform taken along line 4—4 in FIG. 1.

The torsional members 30 and 31 preferably comprise a reduction gear assembly 40 (see FIG. 4). The reduction gear assembly 40 comprises a drive nut 42 rotatably captured on the shaft of the spreader arm 18 or 19, a first shaft 45 axially extending from the spreader arm 18 or 19, and a second shaft 47 extending from the torque base 32 or 33, the second shaft 47 is rotatably captured over the first shaft 45 by a shoulder screw 49.

The drive nut 42 preferably has a beveled face 43 that is adjacent to an end of the second shaft 47. A wobble plate mounted on the first shaft 45 interposes the drive nut 42 and the second shaft 47. The wobble plate 44 is captured in splines 46 on the first shaft 45 to prevent the wobble plate 44 from rotating relative to the first shaft 45. The splines 46, however, do not restrict the wobble plate's 44 wobble motion.

The wobble plate 44 and the second shaft 47 include opposing operably connected face gears 41 and 48, respectively. The face gear 41 on the wobble plate 44 only meshes fully at one point with the face gear 48 on the second shaft 47 as the wobble plate 44 wobbles from the rotation of the drive nut 42. Thus, the interaction between the face gears 41 and 48 creates a gear ratio between the drive nut 42 and the second shaft 47 that is preferably in the range of about 60–80:1. Accordingly, only a relatively low torque is necessary to turn the drive nut 42 to rotate the second shaft 47, in either direction and, thus, rotate the torque base 32 and 33 with a torque necessary to vertically displace a patient's ribs with blades 50 and 51 and to depress a patient's sternum with the support pads 80 and 81.

Alternatively, the torsional members 30 and 31 could comprise a ratchet mechanism, a wrap spring mechanism or a lock nut mechanism (not shown) wherein a wrench or a special tool could be used to rotate the torque bases 32 and 33 to a desired position. Once the torque bases 32 and 33 are rotated to their desired positions, they are prevented from reverse rotation by the ratchet, wrap spring or lock nut mechanism.

Figure 5:
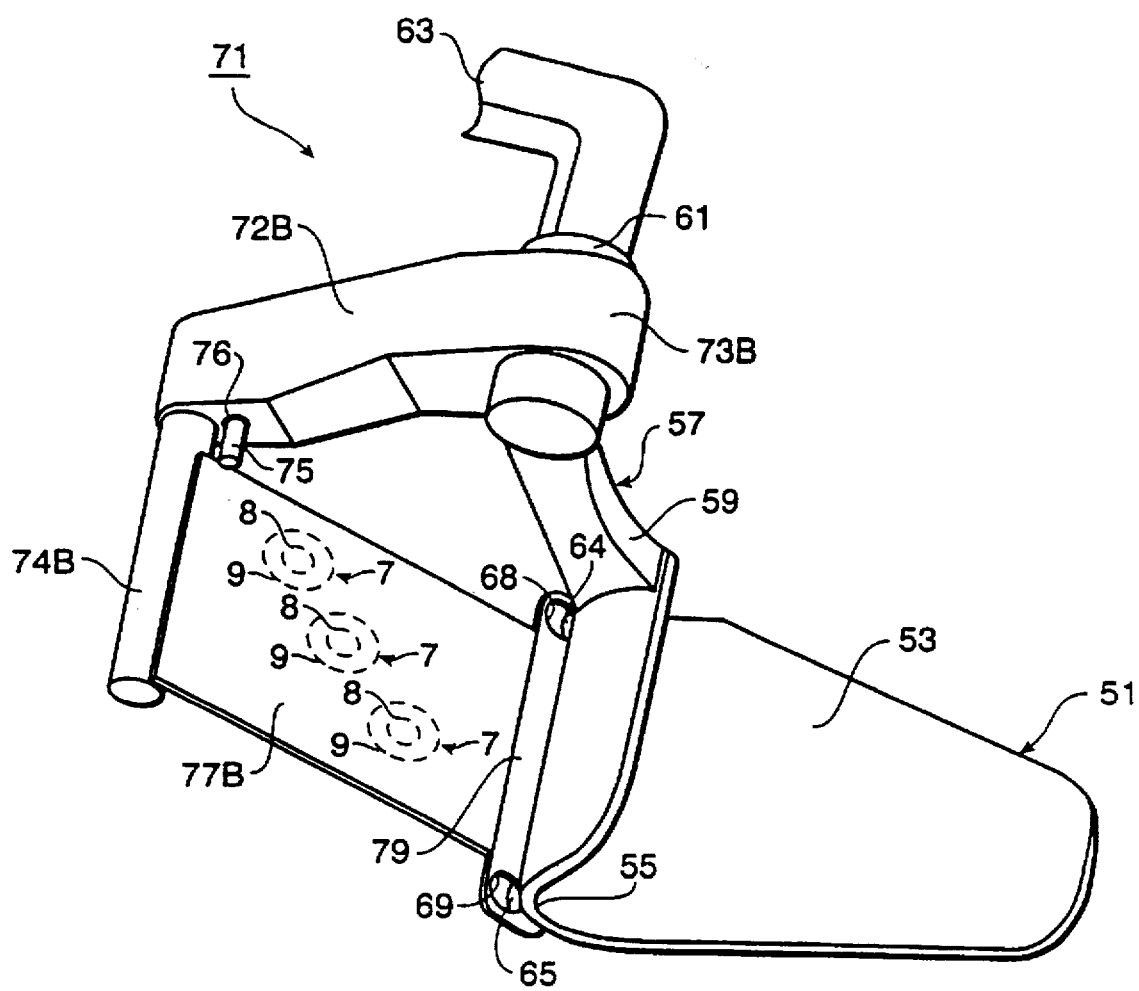
FIG. 5 is an isometric view of a blade, a blade arm and a tissue retractor assembly of the access platform shown in FIG. 1.
Figure 6:
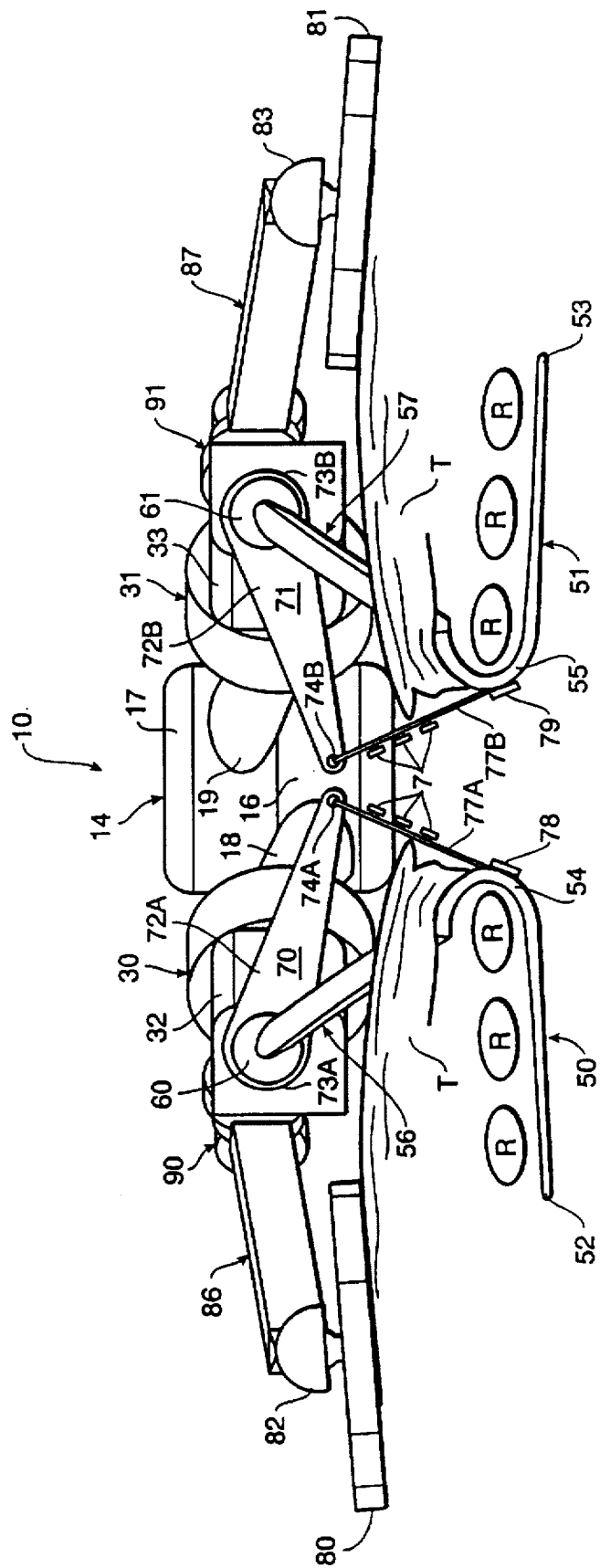
FIG. 6 is a front view of the access platform with the tissue retractors disengaged.
Figure 7:
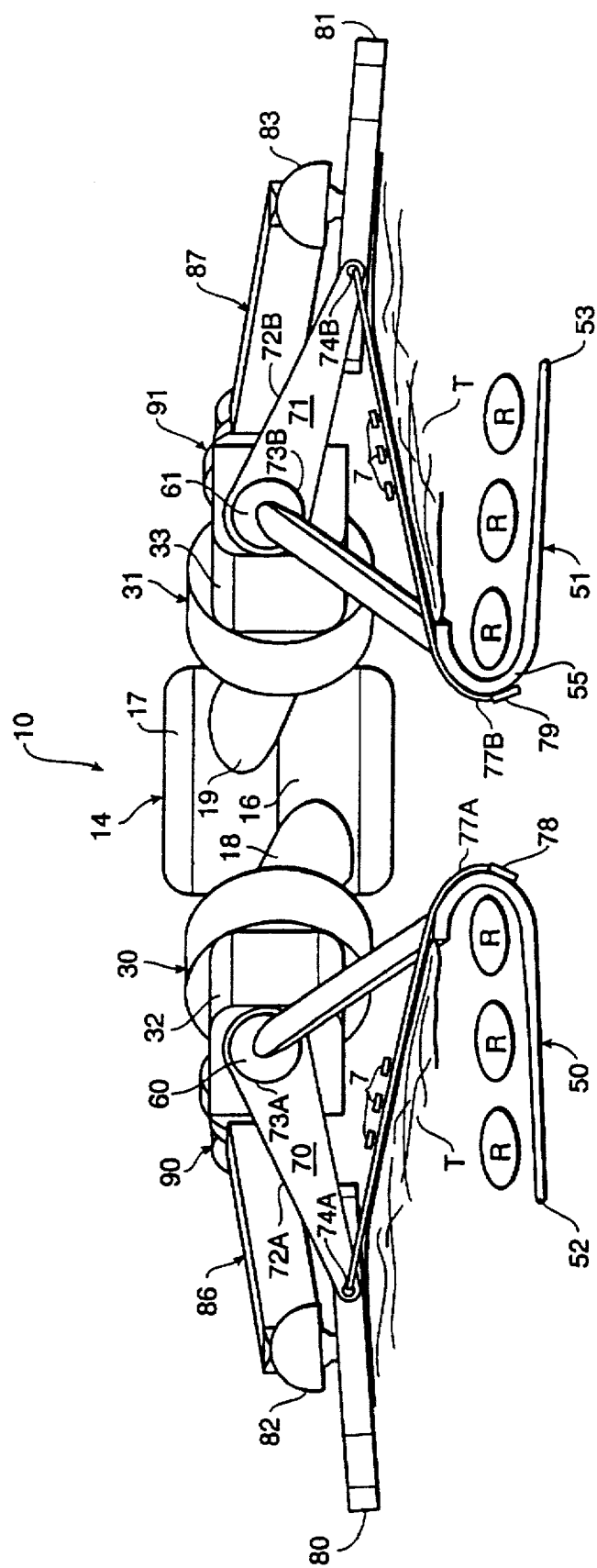
FIG. 7 is a front view of the access platform with the tissue retractors engaged.

Turning to FIGS. 5–7, the tissue retractor 70 and 71 comprise arms 72A and 72B extending from hubs 73A and 73B. The hubs 73A and 73B are rotatably mounted on the pivots 60 and 61 of the blade arms 56 and 57. At an end opposite to the hubs 73A and 73B, spindles 74A and 74B extend from the arms 72A and 72B. Elastic sheets 77A and 77B, preferably constructed from natural latex rubber, attach at one end to the spindles 74A and 74B, and at the opposite end to attachment plates 78 and 79. Slots 68 and 69 in the attachment plates 78 and 79 enable the attachment plates 78 and 79 to connect to the blades 50 and 51 by communicating with hooks 64 and 65 extending from the blades 50 and 51. Locking pin 75 is attached in a parallel manner to the spindle 74B. The locking pin 75 communicates with recess 76 in the arm 72B such that the spindle 74B can be rotated to take up excess slack in the elastic sheet 77B and, then, locked in place by mating the locking pin 75 with the recess 76. A locking pin (not shown) is attached to the spindle 74A and a recess (not shown) is formed in the arm 72A. Alternatively, the arms 72A and 72B would include a plurality of recesses (not shown) for greater adjustability.

The tissue retractors 70 and 71 include a plurality of low profile button cleats 7 formed in the top surface of the elastic sheets 77A and 77B. The cleats 7 include a stem 8 that extends upwardly from the elastic sheets 77A and 77B and a cap 9 that attaches to the stem 8. In operation, the surgeon can anchor sutures to the cleats 7 which the surgeon would normally anchor to the patient's chest.

Referring to FIG. 1, the access platform 10 preferably includes a port 66 mounted on either arm 56 adjacent to the pivot 60. The port 66 can be used to mount a heart stabilizer instrument 67 for which a patent application is being concurrently filed. Additional ports located on the other blade arm 57 adjacent the pivot 61 or located adjacent to the blades 50 and 51 on both blade arms 56 and 57, may be desirable to mount other surgical instruments used in a "beating heart" CABG procedure, such as a scope for IMA take down, an IMA holder used to hold the IMA during the installation of the graft or a suture holder. The mounting of these instruments to the access platform 10 advantageously eliminates the need for an additional set of hands around the surgical site.

In operation, the blades 50 and 51 are positioned within the incision in the patient's chest P such that the vanes 52 and 53 slide under the patient's ribs R (see FIGS. 6 and 7). The throats 54 and 55 of the blades 50 and 51 receive and substantially surround the opposing ribs proximal to the incision in the patient's chest P. Once the blades 50 and 51 are in position, the blades 50 and 51 are connected to the rest of the access platform 10 by inserting the stems 62 and 63 of the blade arms 56 and 57 into the sockets 34 and 35 in the torque bases 32 and 33.

Next, the hub 14 of the spreader member 12 is rotated to laterally spread the spreader arms 18 and 19 apart until the blades 50 and 51 have retracted the patient's ribs R to a desired spacing. The support pads 80 and 81 are then lowered to rest on the patient's chest and locked in place with lock positioners 90 and 91. At this point, the torque bases 32 and 33 are rotated relative to the torsional members 30 and 31 to displace in an essentially vertical direction the blades 50 and 51, and ultimately the patient's ribs R, relative to each other.

As the blade 51 is raised, the corresponding support pad 81 depresses the patient's sternum to further cause a greater deflection in the patient's rib cage and, thus, increase the "tunnel" effect. The elongated vane construction of the blades 50 and 51 advantageously enables the access platform 10 to vertically raise a plurality of the patient's ribs R to cause a greater "tunnel" effect under a patient's rib cage and, thus, increases the surgeon's working area and visual access to the IRA. The recessed throat construction of the blades 50 and 51 advantageously enables the access platform 10 to vertically displace the opposite rib that is proximal to the chest incision downwardly to further increase the surgeon's visual access. This combined motion helps to create an optimum tunnel.

After the ribs have been offset, the tissue retractors 70 and 71 are operated to retract the soft tissue T away from the incision area by rotating the arms 72A and 72B about the pivots 60 and 61 on the blade arms 56 and 57 (See FIGS. 6 and 7). By rotating the arms 72A and 72B about the pivots 60 and 61, the elastic sheets 77A and 77B advantageously grab, pull and press down against the soft tissue T proximal to the incision to retract it away from the incision and out of the surgeon's working area. The over-center positioning of the arms 72A and 72B about the hubs 73A and 73B, effectively locks the tissue retractors 70 and 71 in place during use.

In a first offset position, the blade 51 raises the retracted ribs and the blade 50 depresses the retracted ribs so that the surgeon can take down the proximal portion of the IMA. Next, the blades 50 and 51 are rotated to a second offset position wherein the blade 50 raises the retracted ribs and the blade 51 depresses the retracted ribs. In this offset position, the surgeon takes down the distal portion of the IMA. With the dissection of the IMA complete, the surgeon levels the blades 50 and 51 and then engages the heart stabilizer 67. With the heart stabilizer 67 engaged to minimize the movement of the heart, the surgeon performs an arteriotomy and an anastomosis. After completion of the arteriotomy and anastomosis, the surgeon removes the stabilizer 67, buttons up the pericardial sac, disengages the soft tissue retractors 70 and 71 and brings the blades 50 and 51 together. The blades 50 and 51 are then disengaged from the access platform 10 and removed from the interior of the patient's chest. With the blades 50 and 51 removed, the surgeon is able to sew up the thoracotomy and complete the surgical procedure.

Figure 8:
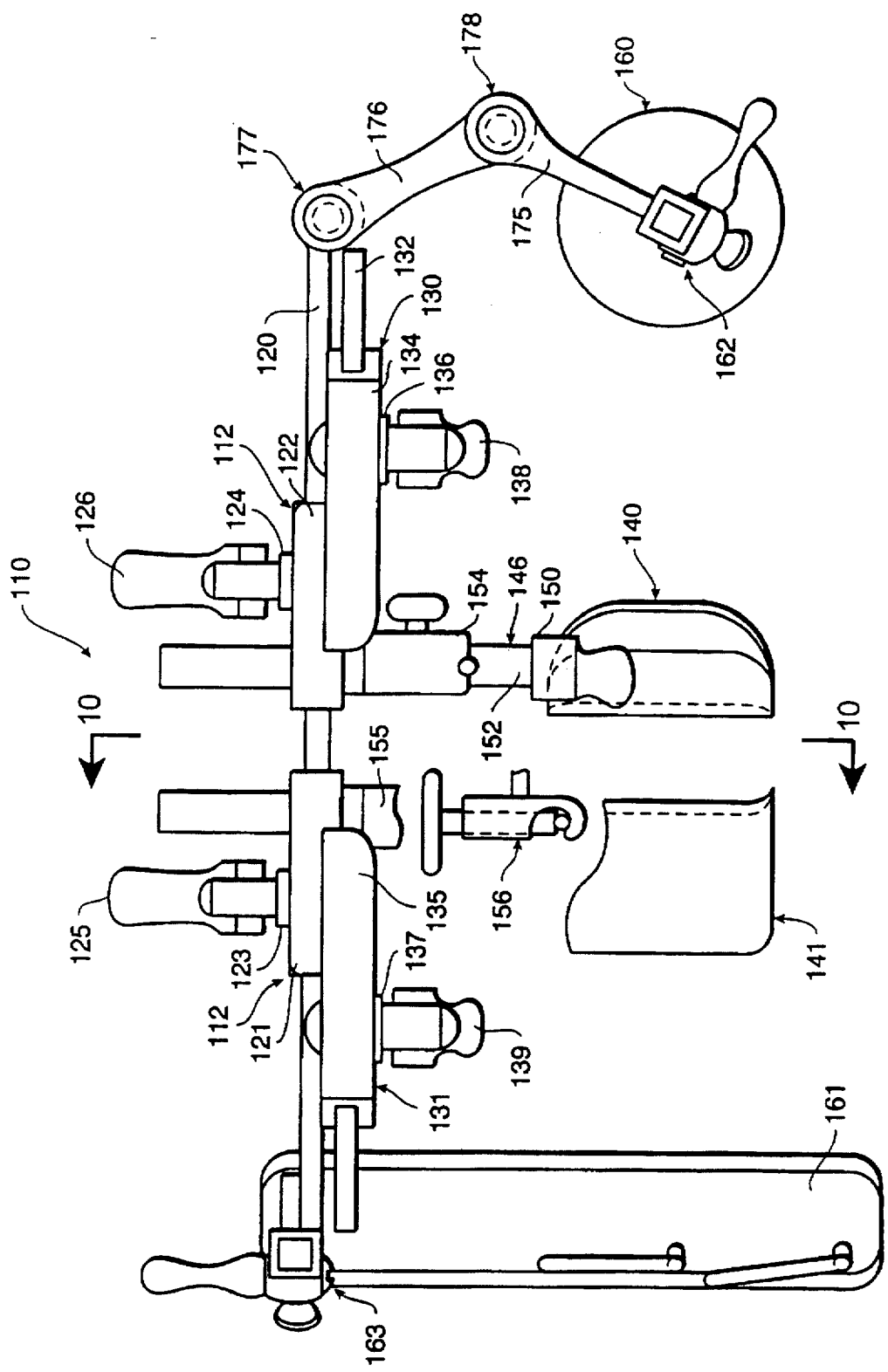
FIG. 8 is a top view of a second embodiment of the access platform,of the present invention.
Figure 9:
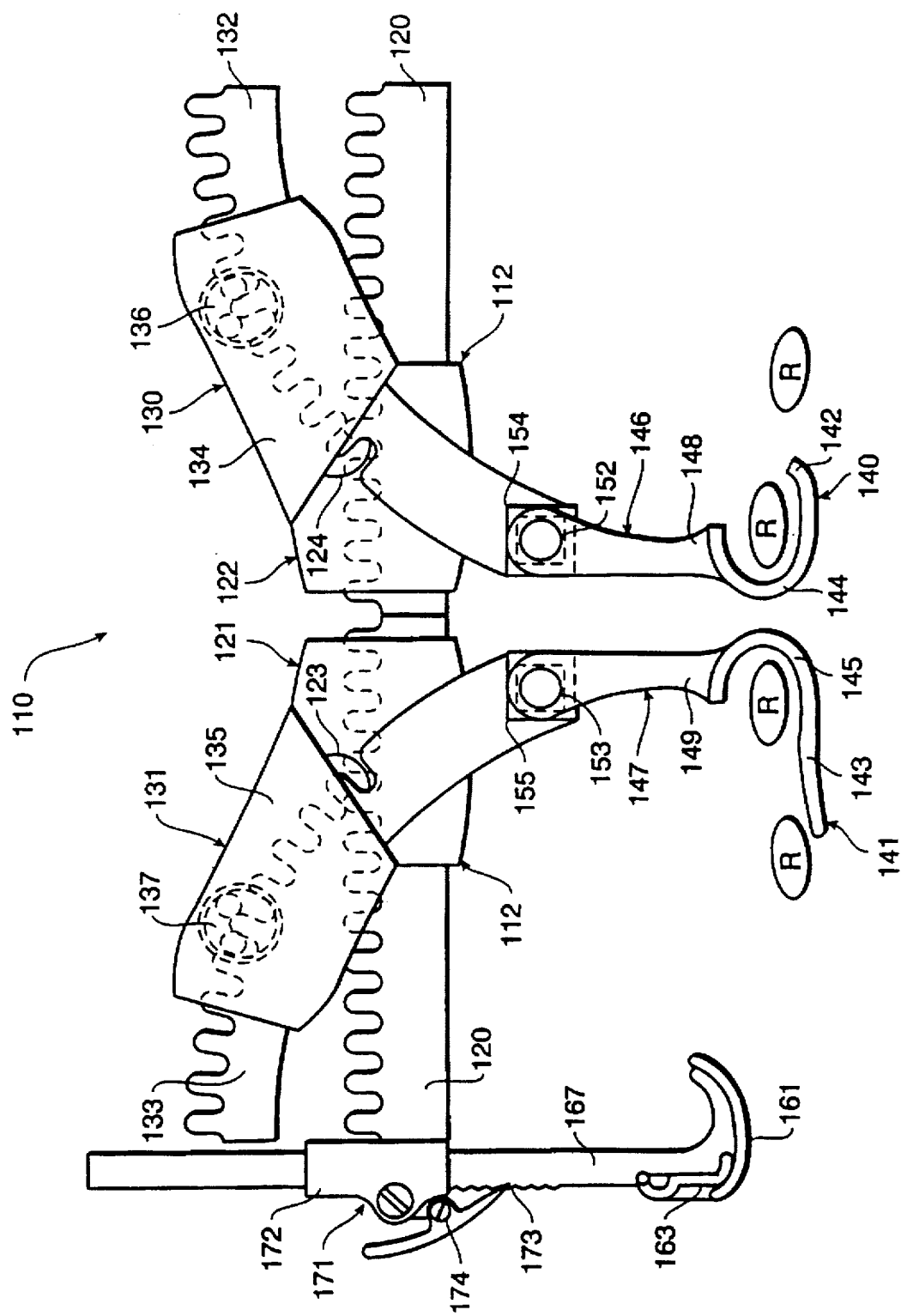
FIG. 9 is a partial front view of the access platform shown in FIG. 8.
Figure 10:
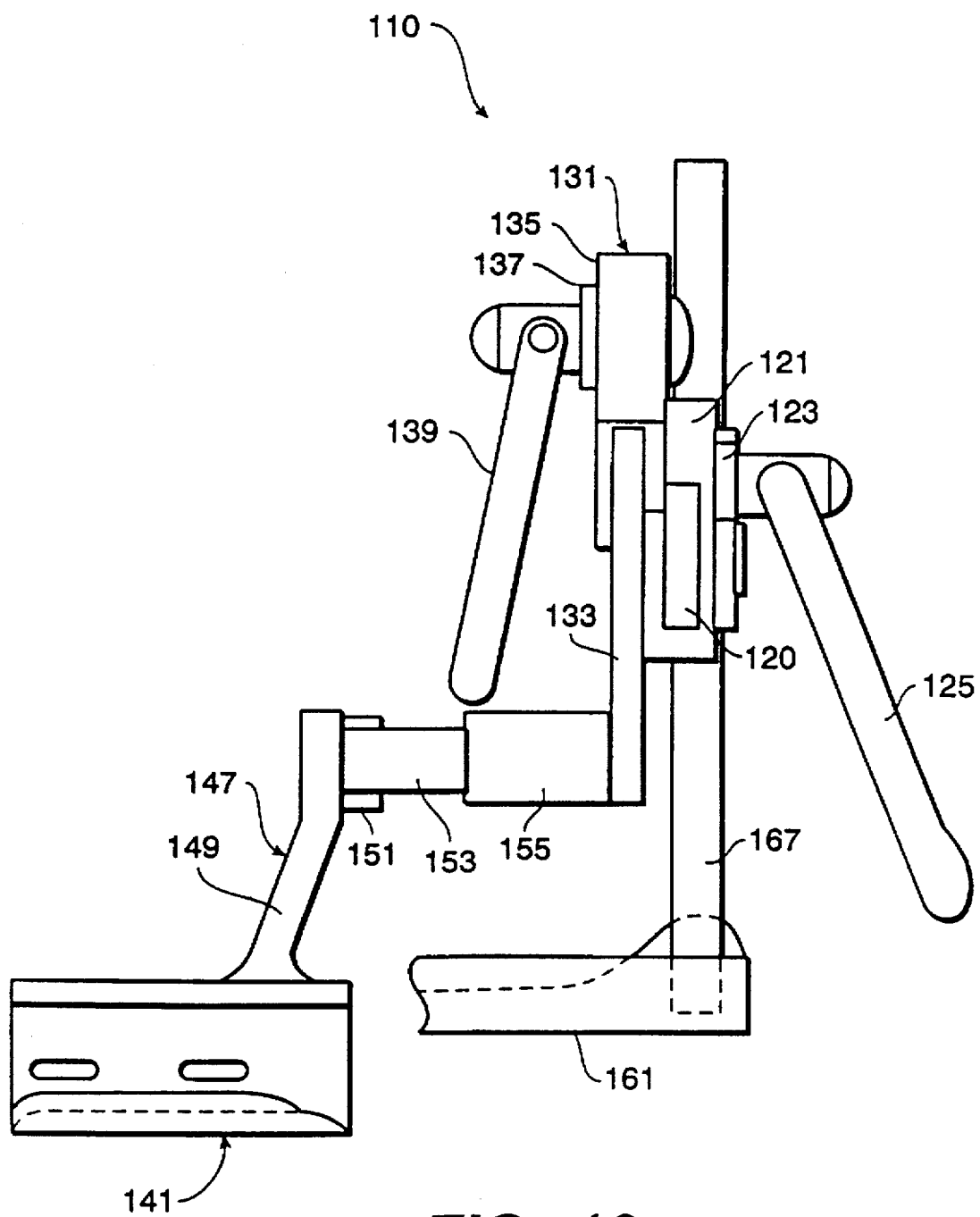
FIG. 10 is a side view of the access platform as viewed along a line 10—10 in FIG. 8.

A second embodiment of the access platform 110 is shown in FIGS. 8, 9 and 10. The second embodiment of the access platform 110 includes a spreader member 112 preferably comprising a horizontally disposed rack 120 and pinion housings 121 and 122 slidably disposed over the rack 120. The pinion housings 121 and 122 rotatably retain pinions 123 and 124 driven by levers 125 and 126.

Torsional members 130 and 131 preferably comprise curved racks 132 and 133 slidably received within pinion housings 134 and 135. The pinion housings 134 and 135 are fixedly attached to the pinion housings 122 and 121. The pinion housings 134 and 135 rotatably retain pinions 136 and 137 driven by levers 138 and 139. Sockets 154 and 155 are formed in the lower ends of the curved racks 132 and 133. Stems 152 and 153 of blade arms 146 and 147 are releasably received by and horizontally extend from sockets 154 and 155.

The blade arms 146 and 147 further comprise pivot sections 150 and 151 extending horizontally from stems 152 and 153. Branches 148 and 149 extend downwardly and outwardly from the pivot sections 150 and 151 of blade arms 146 and 147 to position the remainder of the access platform 110 away from the surgeon's working area. Branches 148 and 149 attach to blades 140 and 141. Blades 140 and 141 comprise elongated vane sections 142 and 143 extending outwardly from recessed throat sections 144 and 145.

Preferably, one end of the horizontally disposed rack 120 is connected to a slide 172 of a lock positioner 171. The slide 172 is slidably received over a vertically disposed support pad stanchion 167. The stanchion 167 has ratchet gear teeth 173 formed thereon which cooperate with a ratchet lever 174 attached to the slide 172 to adjustably position the support pad 161. The support pad 161 is adjustably connected to the stanchion 167 by a swivel connector 163.

The opposing end of the horizontally disposed rack 120 is preferably connected to a support pad link 176 via a lockable ball and socket joint 177. The support pad link 176 is further connected to a second support pad link 175 via a hinge joint 178. This link and joint assembly allows for multiple positioning of the support pad 160. Support pad 160 is further connected to the support pad link 175 via a swivel connector 162.

In addition, the access platform 110 includes a mount 156, attached to the blade arm 147. The mount 156 enables the access platform 110 to hold a heart stabilizer tool 67 shown in FIG. 1, an IMA holder, an IMA scope, a suture holder, or other surgical instruments used in a "beating heart" CABG procedure. Thus, the mount 156 advantageously eliminates the need for an undesirable extra set of hands around the surgical site.

In operation, blades 140 and 141 are inserted in an incision in the patient's chest such that the blade vanes 142 and 143 slide under the patient's ribs and the recessed throats 144 and 145 of blades 140 and 141 receive the ribs that are proximal to the incision. After the blades 140 and 141 are properly positioned, the stems 152 and 153 of the blade arms 146 and 147 are inserted into the sockets 154 and 155 of the torsional members 130 and 131 to connect the blades 140 and 141 to the remainder of the access platform 110. Levers 126 and 125 are then rotated to drive the pinions 121 and 122 over the rack 120 to laterally retract the ribs. When a desired spacing between the retracted ribs is met, the support pads 160 and 161 are positioned on the chest of the patient, with support pad 160 being preferably positioned on the patient's sternum. The levers 138 and 139 then are rotated to drive pinions 136 and 137 to draw the curved racks 132 and 133 through the pinion housing 134 and 135 to vertically displace the blades 140 and 141 and the retracted ribs. As the blade 140 is retracted upwards the support pad 160 preferably depresses the sternum creating a greater deflection in the patient's rib cage and, thus, creating a greater "tunnel" effect underneath the patient's rib cage, to increase the surgeon's working space and visual access for dissection of the IMA.

As in the first embodiment, after the ribs have been vertically displaced, tissue retractors 70 and 71 (shown in FIGS. 5–7) are operated to retract the soft tissue away from the incision area by rotating the arms 72A and 72B about the pivots 150 and 151 on the blade arms 146 and 147. By rotating the arms 72A and 72B about the pivots 150 and 151, the elastic sheets 77A and 77B advantageously grab, pull, and press down against the soft tissue to retract it away from the incision and out of the surgeon's working area.

In a first offset position, the blade 141 would raise the retracted ribs and the blade 140 would depress the retracted ribs so that the surgeon can take down the proximal portion of the IMA. Next, the blades 140 and 141 are rotated to a second offset position wherein the blade 140 lifts the retracted ribs and the blade 141 depresses the retracted ribs. In this offset position, the surgeon takes down the distal portion of the IMA. With the dissection of the IMA complete, the surgeon levels the blades 140 and 141 and then engages the heart stabilizer 67. With the heart stabilizer 67 engaged to minimize the movement of the heart, the surgeon performs an arteriotomy and anastomosis. After completion of the arteriotomy and anastomosis, the surgeon removes the stabilizer 67, buttons up the pericardial sac, disengages the soft tissue retractors 70 and 71 and brings the blades 140 and 141 together. The blades 140 and 141 are then disengaged from the access platform 10 and then removed from the interior of the patient's chest. With the blades 140 and 141 removed, the surgeon is able to sew up the thoracotomy and complete the surgical procedure.

Figure 11:
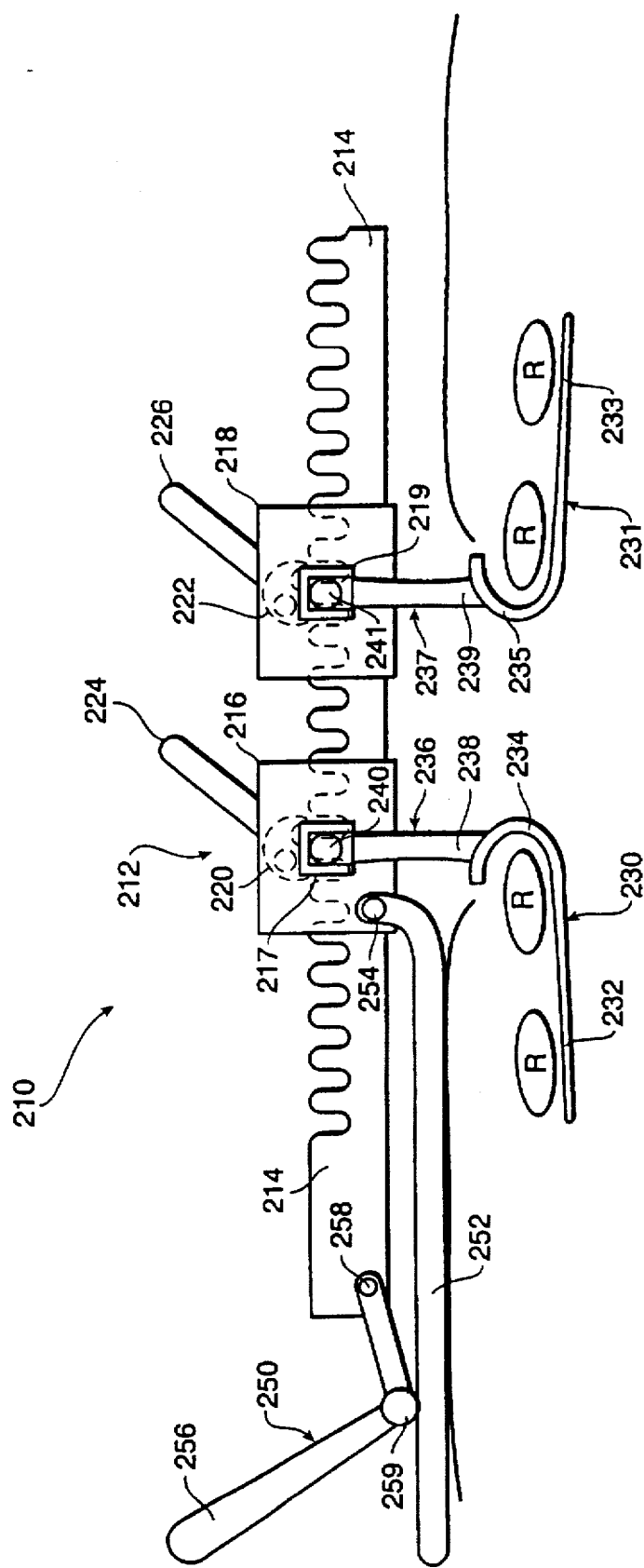
FIG. 11 is a front view of a third embodiment of the access platform of the present invention.
Figure 12:
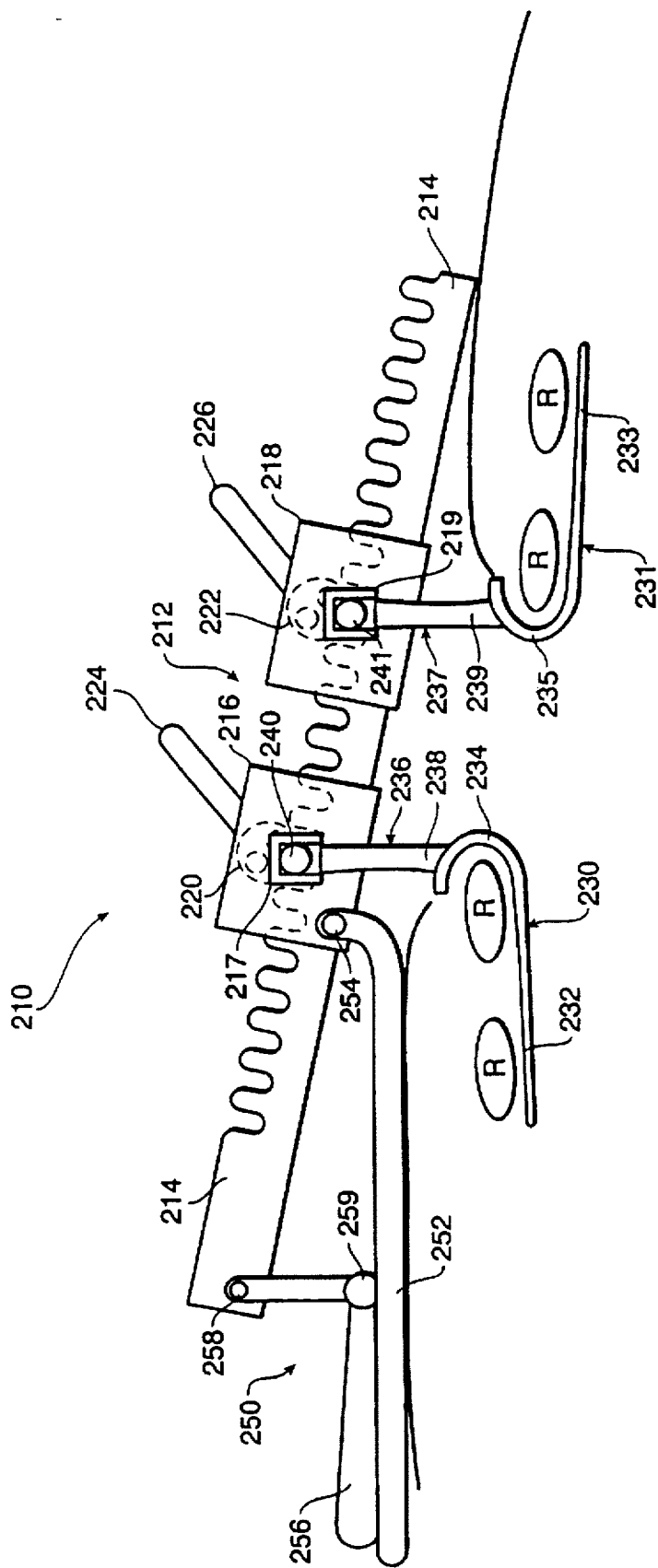
FIG. 12 is a front view of the access platform shown in FIG. 11 with the torsional member engaged.

A third embodiment of the access platform 210 is shown in FIGS. 11 and 12. The third embodiment of the access platform 210 includes a spreader member 212 comprising a horizontally disposed rack 214 and pinion housings 216 and 218 slidably disposed over the rack 214. Pinions 220 and 222 are rotatably retained in the pinion housings 216 and 218 and driven by levers 224 and 226.

Blades 230 and 231 comprise elongated vane sections 232 and 233 extending from recessed throat sections 234 and 235. Blade arms 236 and 237 have branches 238 and 239 which extend downwardly and outwardly from horizontally disposed stems 240 and 241. The stems 240 and 241 of the blade arms 236 and 237 are releasably received in sockets 217 and 219 in the pinion housings 216 and 218.

A torsional member 250 comprises a support pad 252 pivotally connected to the pinion housing 216 at a pivot 254 and extends laterally away from the pinion housing 216. An "L"-shaped lever 256 is pivotally connected to a rack 214 at a pivot 258 on the end of the short leg of the "L"-shaped lever 256. A slide 259 is formed at the intersection of the short and long legs of the "L"-shaped lever 256. The slide 259 slidably contacts the support pad 252.

In operation, the blades 230 and 231 are inserted into the chest incision and positioned such that the vane sections 232 and 233 slide under the patient's ribs R and the recess throat sections 234 and 235 receive the patient's ribs R proximal to the incision. Once the blades 230 and 231 are properly in place, the stems 240 and 241 of the blade arms 236 and 237 are inserted into the sockets 217 and 219 of the pinion housings 216 and 218. Next, the levers 224 and 226 are rotated to drive pinions 220 and 222 along the rack 214 to laterally retract the ribs. The "L"-shaped lever 256 is then rotated downwardly toward the patient's chest such that the slide portion 259 slides along the support pad 252 while the "L"-shaped lever 256 pivots about the pivot 258. As a result, one end of the rack 214 is raised to vertically offset blade 230 relative to 231.

As with the first two embodiments, the tissue retractor 70 and 71 can be used with this embodiment of the access platform 210 to retract soft tissue away from the incision and the surgeon's working area.

Figure 13:
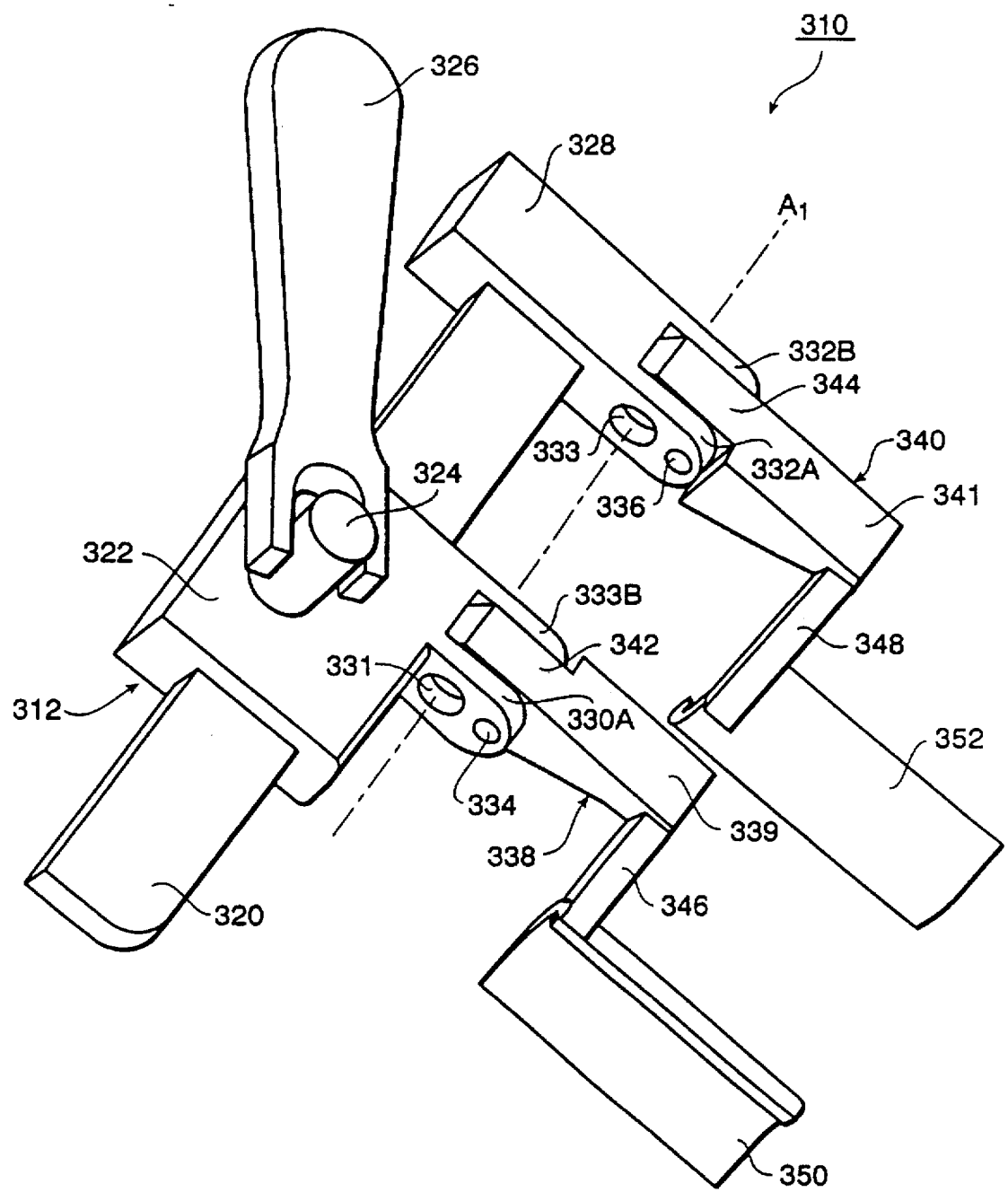
FIG. 13 is an isometric view of a fourth embodiment of the access platform of the present invention.
Figure 14:
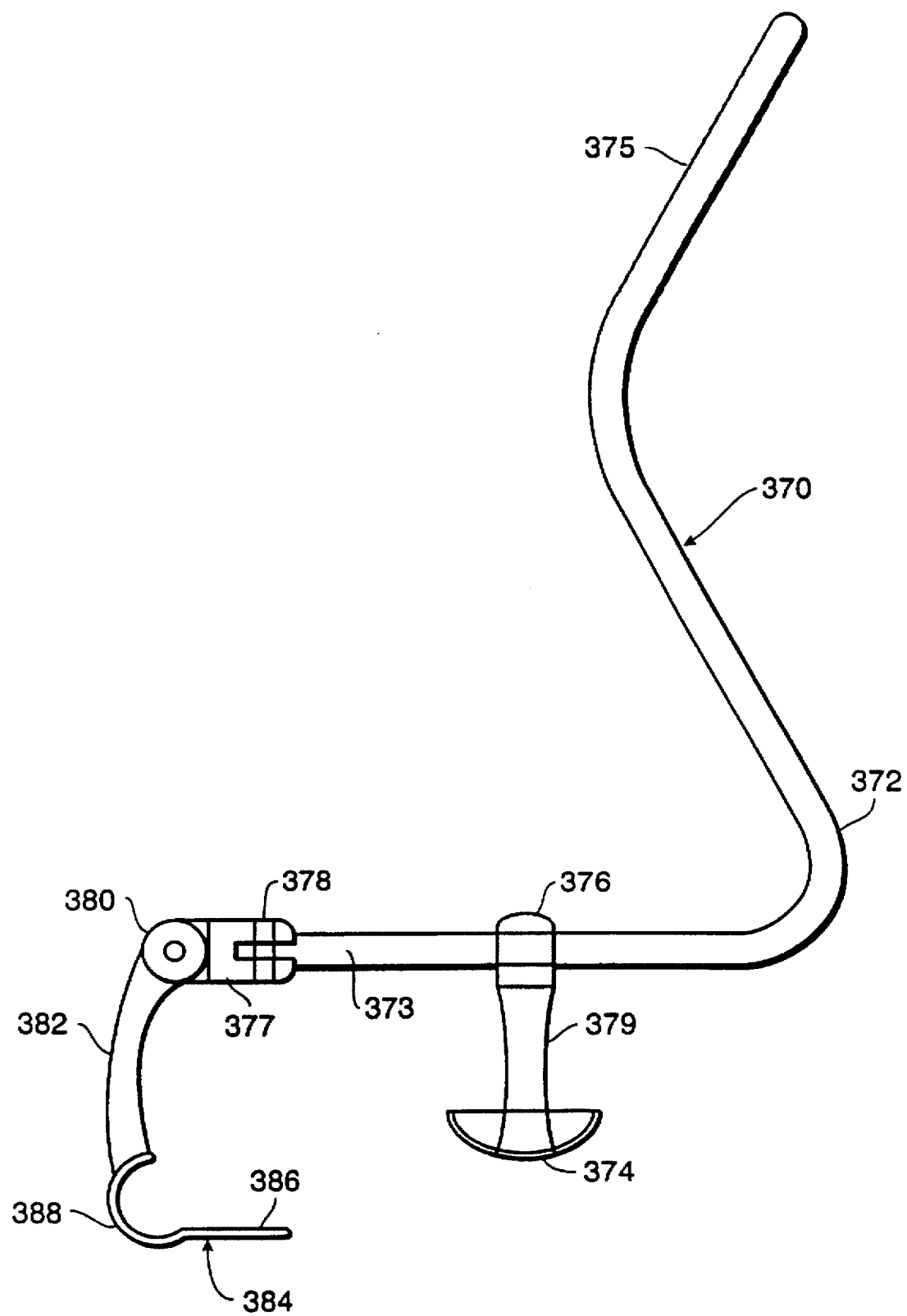
FIG. 14 is an elevation view of a pry bar engaging the blade arm of the access platform in FIG. 13.
Figure 15:
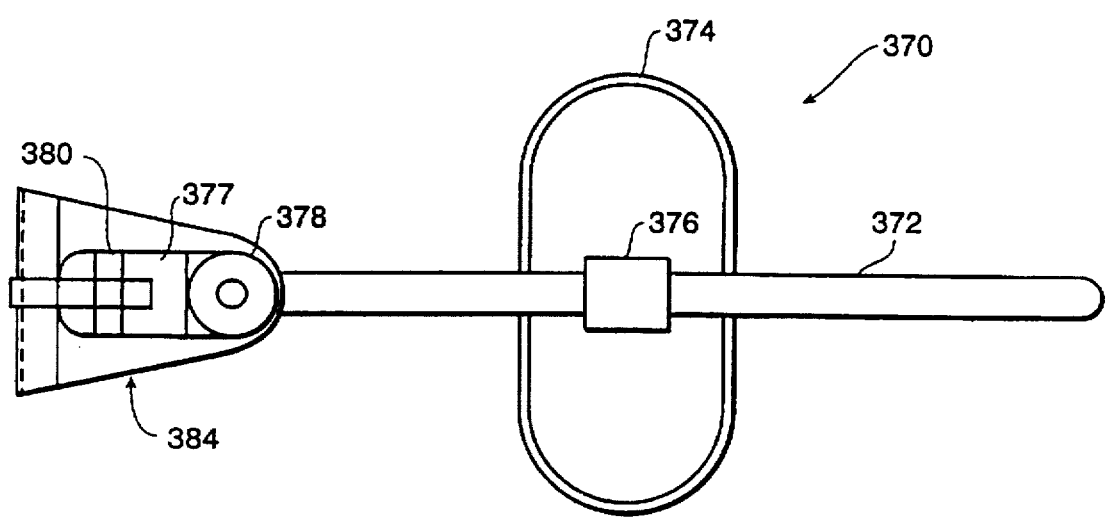
FIG. 15 is a top view of the pry bar.

A fourth embodiment is shown in FIGS. 13–15. The access platform 310 of the fourth embodiment includes a spreader member 312 comprising a rack 320, a housing 322 slidably received over the rack 320, a pinion 324 rotatably retained in the housing 322 and a lever 326 connected to the pinion 324. A spreader base 328 is attached to one end of the rack 320. A pair of parallel spaced fingers 330A and 330B extend from the housing 322. Similarly, a pair of parallel spaced fingers 332A and 332B extend from the spreader base 328 and are positioned parallel to the fingers 330A and 330B extending from the housing 322.

A pair of blade arms 338 and 340 include branch sections 346 and 348 that extend downwardly from central portions 339 and 341 and connect to blades 350 and 352. Stem portions 342 and 344 extend from the central portions 339 and 341 opposite the branch sections 346 and 348. The stem 342 extends between and is pivotally mounted to fingers 330A and 330B at a pivot 331. Likewise, stem 344 extends between and is pivotally mounted to fingers 332A and 332B at a pivot 333. As a result, the blade arms 338 and 340 rotate about an axis of rotation $A_i$ that is parallel to the rack 320. This construction advantageously enables the access platform 310 to address a thoracotomy positioned anywhere along the chest wall without intruding on the surgeon's working space. If the thoracotomy is located on the lateral side of the chest wall the spreader member 312, the spreader base 328 and the housing 322 are simply pivoted out of the surgeon's way.

However, if desired, locking pins 334 and 336 can be used immobilize the blade arms 338 and 340 and fix them relative to the housing 322 and the spreader base 328.

Turning to FIGS. 14 and 15, a pry bar 370, which is used in conjunction with the access platform 310 to offset a patient's ribs, is shown. The pry bar 370 comprises an "S"-shaped body 372 pivotally connected to a pivot base 377 at pivot 378. The pivot base 377 is in turn pivotally connected to a blade arm 382 at pivot 380. The blade arm 382 extends downwardly from the pivot 380 and connects to a blade 384. The blade 384 includes an elongated vane 386 and a deep recessed throat 388. A sternal pad 374 is connected to a post 379 that slidably connects to the lower portion 373 of the "S"-shaped body 372 via a slide 376.

In operation, the blade 384 is positioned such that the throat 388 captures the blade 350 or 352 of the access platform 310. As the throat 388 captures the blade 350 or 352 the elongated vane 386 extends under a plurality of the patient's ribs to be offset. The pivot base 377 and the pivots 378 and 380 enable the pry bar 370 to be adjustably positioned about two different axes of rotation.

Once the blade 384 is positioned, the sternal pad 374 is adjustably located to atraumatically conform the pry bar 370 to the anatomy of the patient. Once the sternal pad 374 is in position, a handle 375, in the upper portion of the "S"-shaped body 372, is pulled to pivot the pry bar 370 about the sternal pad 374 and lift the blade 384 and the blade 350 or 352 of the access platform 310 to offset the patient's ribs and create a "tunnel" to increase the surgeon's working space and visual access for the dissection of the IMA.

Figure 16:
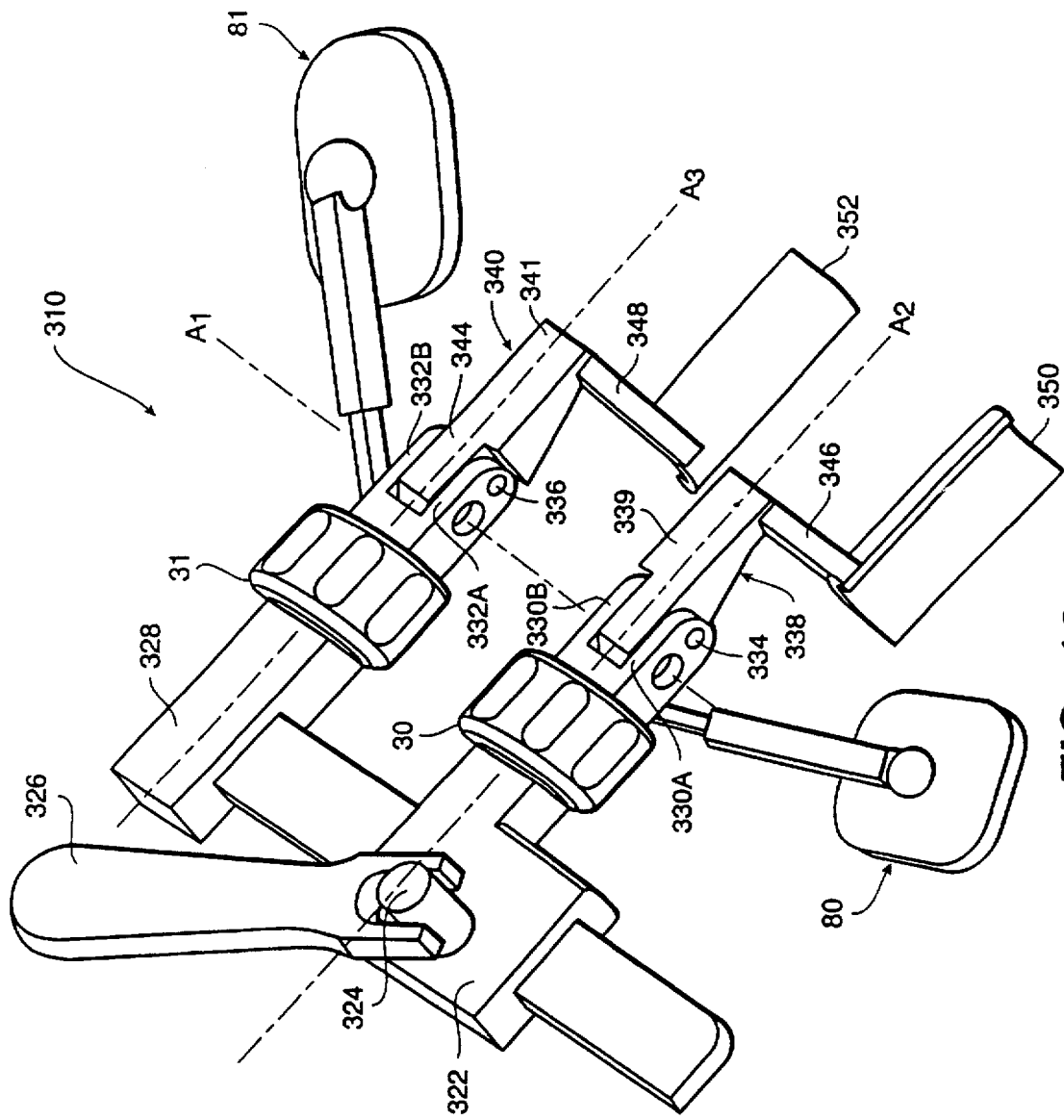
FIG. 16 is an isometric view of a fifth embodiment of the access platform of the present invention.

Alternatively, a fifth embodiment of the access platform 310 is shown in FIG. 16 to comprise a combination of components from the first and fourth embodiments. More particularly, the torsional members 30 and 31 of the first embodiment are interposed between and operably connected to the fingers 330A and 330B and the housing 322, and interposed between and operably connected to the fingers 332A and 332B and the spreader base 328, respectively. In addition, the support pads 80 and 81 of the first embodiment are adjustably attached to the fingers 330A and 332B. By including the torsional members 30 and 31 and the support pads 80 and 81, a second axis of rotation $A_2$ is provided. Thus, as in the first embodiment, the torsional members 30 and 31 enable the access platform 310 to vertically displace the blades 350 and 352 and the retracted ribs.

Also included with the fourth and fifth embodiments of the access platform 310, are ports or mounts (not shown) similar to the port 66 shown in FIG. 1 and similarly used to mount a heart stabilizer 67, an IMA holder, an IMA scope, a suture holder or other surgical instruments used in a "beating heart" CABG procedure. The surgical instrument mounting capability of the access platform advantageously tends to eliminate the need for extra sets of hands around the surgical area.

Figure 17:
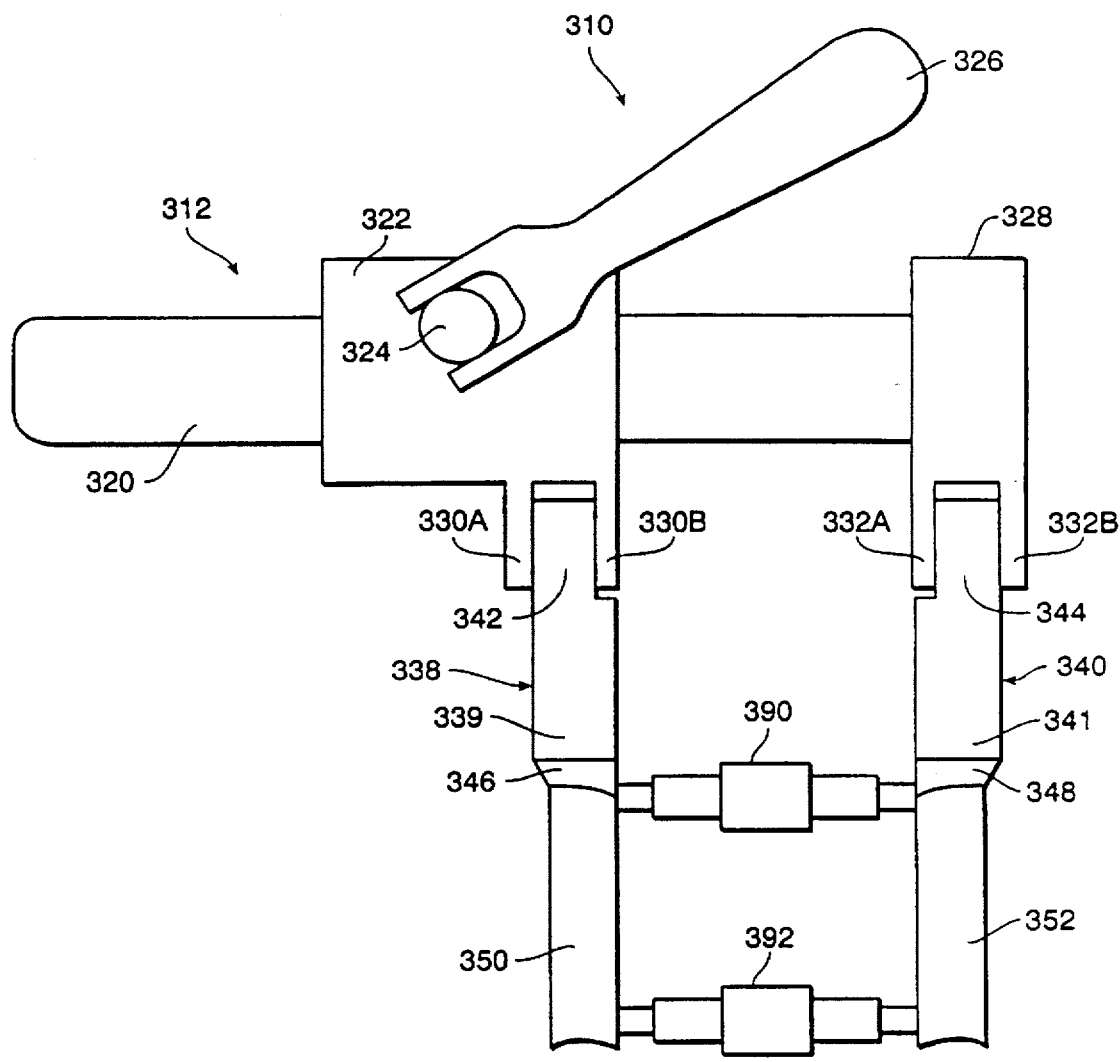
FIG. 17 is a top view of a sixth embodiment of an access platform of the present invention.
Figure 18:
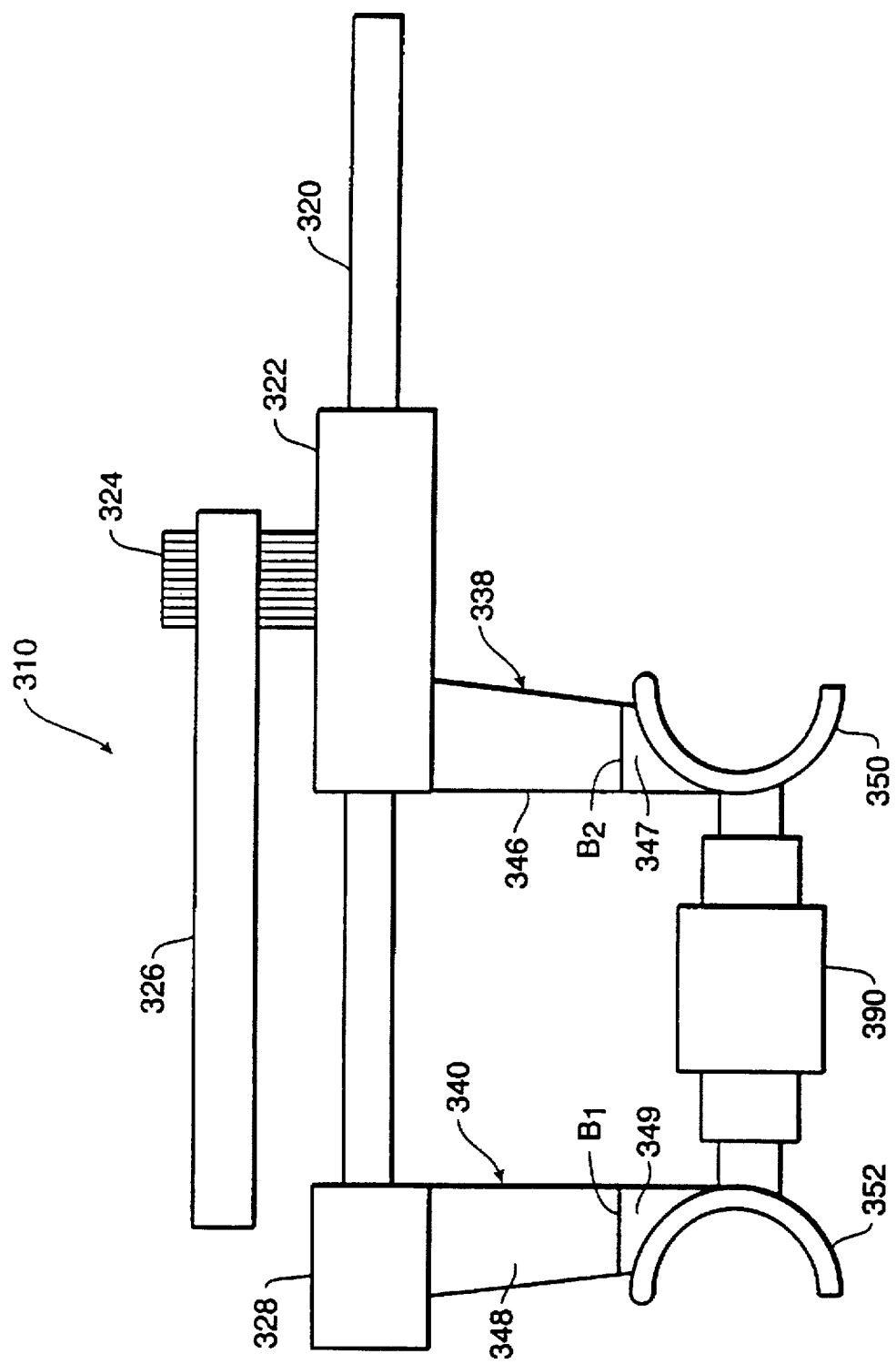
FIG. 18 is a rear view of the access platform in FIG. 17.

Referring to FIGS. 17 and 18, a sixth embodiment of the access platform of the present invention is shown. The sixth embodiment includes the access platform 310 shown in FIG. 13 and telescoping arms 390 and 392 perpendicularly disposed between and releasably attached to the blades 350 and 352. In addition, the blade arms 338 and 340 include branch extensions 347 and 349 releasably coupled at break lines $B_1$ and $B_2$ to the branches 346 and 348.

In operation, the blades 350 and 352 are inserted in an incision in the patient's chest to capture the ribs. The lever 326 is then rotated to drive pinion 324 along the rack 320 and spread the ribs. Once the ribs are retracted to a desired spacing, the telescoping arms 390 and 392 are connected to the blades 350 and 352 and engaged to hold the blades 350 and 352 apart at the desired spacing. The branches 346 and 348 are then decoupled from the branch extensions 347 and 349 and, thus, the remainder of the access platform 310 can advantageously be removed from the surgical site to give the surgeon additional space to work.

Figure 19:
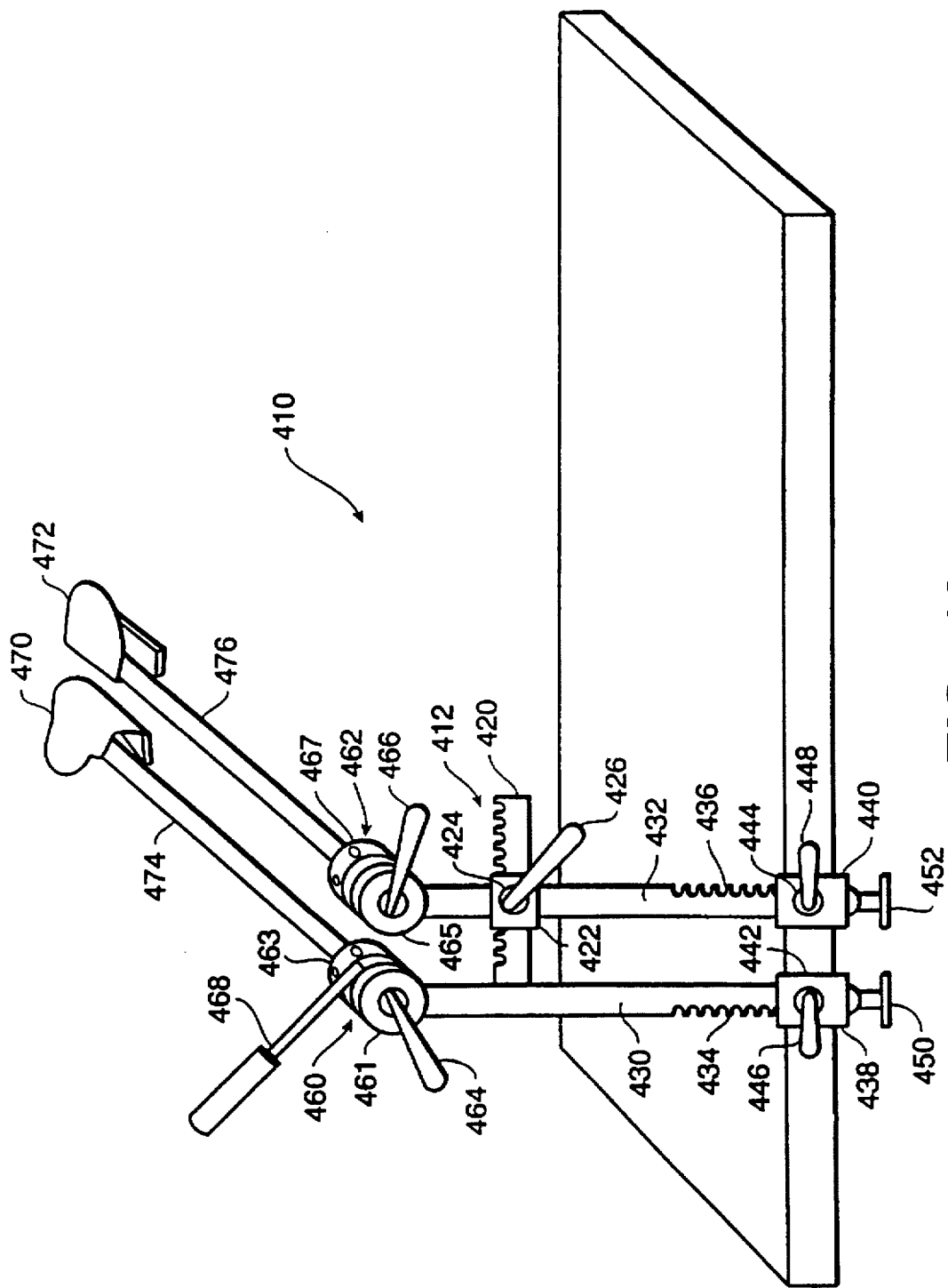
FIG. 19 is an isometric view of a seventh embodiment of an access platform of the present invention.

Turning to FIG. 19, a seventh embodiment of the access platform 410 of the present invention is shown. The access platform 410 mounts to a table or a rail via slides 438 and 440 that are locked in place by positioners 450 and 452. The slides 438 and 440 rotatably retain pinions 442 and 444 driven by levers 446 and 448 and slidably receive stachion racks 430 and 432. The stachion racks 430 and 432 include rack gears 434 and 436 that are operably coupled to pinions 442 and 444. The levers 446 and 448 are rotated to drive the pinions 442 and 444 along the rack gears 434 and 436 to adjust the height of the stachion racks 430 and 432 relative to the table or patient.

A pinion housing 422 is attached to the stachion rack 432 towards its upper end. A rack 420 is attached at one end to the stachion rack 430 and is slidably received in the pinion housing 422. A pinion 424 driven by a lever 426 is rotatably retained in the pinion housing 422 and operably connected to the rack 420. The lever 426 is rotated to drive the pinion 424 along the rack 420 to spread apart the stachion racks 430 and 432 and, effectively, a patient's ribs.

Torsional members 460 and 462 are attached to the top of the stachion racks 430 and 432. Blade arms 474 and 476 extend outwardly from torsional members and attach to blades 470 and 472. The torsional members comprise inner hubs 461 and 465 rotatably received in and operably connected to outer hubs 463 and 467. Locking levers 464 and 466 lock the outer hubs 463 and 467 in place relative to the inner hubs 461 and 465.

In operation, the access platform 410 is positioned such that the blades 470 and 472 can be inserted into an incision in a patient's chest and then attached to the blade arms 474 and 476. Once the blades 470 and 472 are positioned in the incision and attached to the blade arms 474 and 476, the lever 426 is rotated to spread the blades 470 and 472 and the patient's ribs apart. The blades 470 and 472 can be effectively offset by rotating the outer hubs 463 and 467 relative to the inner hubs 361 and 365. A wrench 468 attaches to the outer hubs 463 and 467 to rotate the outer hubs 463 and 467.

Figure 20:
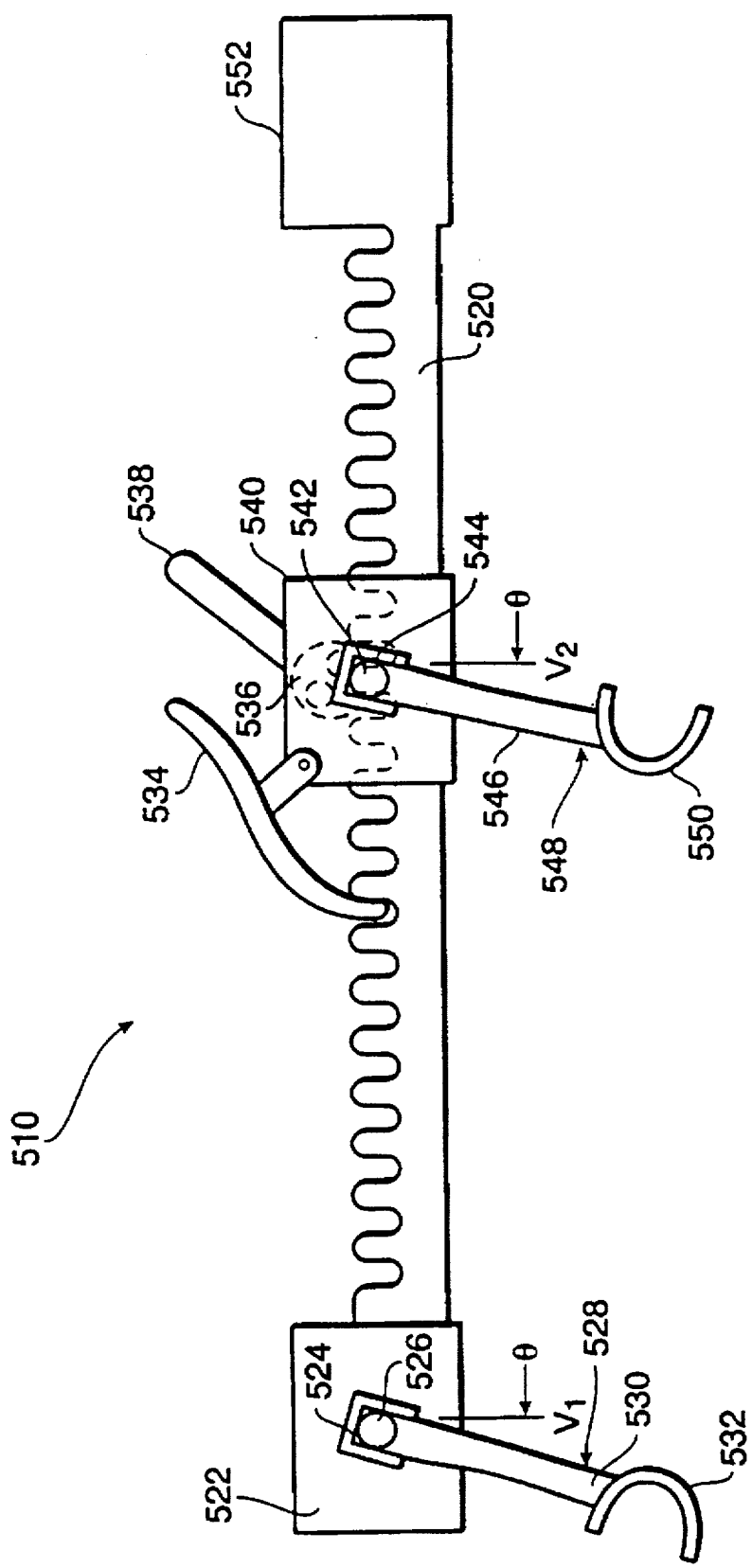
FIG. 20 is a front elevation view of an eighth embodiment of an access platform of the present invention.

Referring to FIG. 20, an eighth embodiment of the access platform 510 of the present invention is shown. The access platform 510 comprises a rack 520 attached at one end to a spreader base 522 and at the other end to a handle 552. A blade 532 is attached to a branch 530 of a blade arm 528. A stem 526 of the blade arm 528 extends from the branch 530 and is releasably received in a socket 524 formed in the spreader base 522. The branch 530 extends downwardly from the stem 526 and is offset to the vertical $V_1$ at an angle $\theta$.

A pinion housing 540 is slidably received over the rack 520 and rotatably retains a pinion 536 driver by a lever 538. The pinion 536 is operably connected to the rack 520.

A blade 550 is attached to a branch 546 of a blade arm 548. A stem 542 of the blade arm 548 extends from the branch 546 and is releasably received in a socket 544 formed in the pinion housing 540. The branch 546 extends downwardly from the stem 542 and is offset to the vertical $V_2$ at an angle $\Phi$.

In operation, the blades 532 and 530 are inserted into an incision in the patient's chest and then the stems 526 and 528 of the blade arms 528 and 548 are inserted into the sockets 524 and 544. The lever 538 is rotated to drive the pinion 536 along the rack 520 until the blades 532 and 550 and the patient's ribs are positioned at a desired spacing. A spring loaded lock lever 534 pivotally mounted to the housing 540 locks the housing 540 in place along the rack 520. The rack 520 is then lifted by the handle 552 to vertically displace or offset the blades 532 and 550 and the patient's ribs.

While the above description contains many specificities, these should not be construed as limitations on the scope of the invention, but rather as an exemplification of one preferred embodiment thereof. Other variations are possible.

Accordingly, the scope of the present invention should be determined not by the embodiments illustrated above, but by the appended claims and their legal equivalents.

What is claimed is:

1. A surgical access platform comprising a spreader member,
    first and second blade interconnected to said spreader member, said first and second blades being adapted to engage opposing sides of a chest incision, with adjustment of said spreader member causing lateral displacement of said first blade relative to said second blade, and
    a displacement member operably interconnected to said first blade and said spreader member, with adjustment of said displacement member causing generally vertical bi-directional displacement of said first blade relative to said second blade.

2. The surgical access platform of claim 1, further comprising a support pad interconnected to said first blade.

3. The surgical access platform of claim 2, wherein said support pad is adjustably interconnected to said first blade.

4. The surgical access platform of claim 1, further comprising a first support pad and a second support pad interconnected to said first and second blades respectively.

5. The surgical access platform of claim 1, wherein said spreader member further comprises a hub.

6. The surgical access platform of claim 5, wherein said hub further comprises an upper hub rotatably connected to a lower hub.

7. The surgical access platform of claim 5, wherein said hub further comprises a ratchet mechanism operably interconnecting a first hub member to a second hub member.

8. The surgical access platform of claim 5, wherein said hub further comprises a harmonic gear assembly operably interconnecting a first hub member to a second hub member.

9. The surgical access platform of claim 6, further comprising first and second spreader arms extending from said upper and lower hubs respectively.

10. The surgical access platform of claim 1, wherein said spreader member further comprises a rack and pinion assembly.

11. The surgical access platform of claim 10, wherein said rack and pinion assembly further comprises
    a pinion housing slidably received over said rack and interconnected to said first blade, and
    a pinion wrench rotatably received in said pinion housing and operably connected to said rack.

12. The surgical access platform of claim 1, wherein said first blade further comprises an elongated vane.

13. The surgical access platform of claim 1, wherein said first blade further comprises a recessed throat.

14. The surgical access platform of claim 1, wherein the displacement member further comprises a first member operably connected to a second member.

15. The surgical access platform of claim 14, wherein said first member further comprises a reduction gear.

16. The surgical access platform of claim 14, wherein said first member further comprises a ratchet mechanism.

17. The surgical access platform of claim 14, wherein said first and second members further comprises a curved rack and pinion assembly.

18. The surgical access platform of claim 1, further comprising a tissue retractor operably interconnected to said first blade.

19. The surgical access platform of claim 1, further comprising a blade arm extending from said first blade and operably connected to said torsional member.

20. The surgical access platform of claim 19, further comprising a tissue retractor pivotally connected to said blade arm and connected to said first blade.

21. The surgical access platform of claim 1 further comprising
    first and second elongated stanchions coupled to said first and second blades, respectively, and said spreader member, said first stanchion being operably coupled to said displacement member, said first stanchion being adjustable in a lateral direction relative to said second stanchion, said first blade being displaceable in a generally vertical direction relative to said second blade.

22. The access platform of claim 21, further comprising
    first and second rotational members mounted adjacent the top of said first and second stanchions, and
    first and second blade arms extending outwardly from said first and second rotational members and connecting to said first and second blades.

23. The surgical access platform of claim 1, further comprising a second displacement member interconnected to said second blade and said spreader member.

24. The surgical access platform of claim 1, further comprising
   a blade arm connected to said second blade and interconnected to said spreader member, and
   a surgical instrument attached to said blade arm and extendable into the chest cavity through a chest incision.

25. The surgical access platform of claim 24, wherein said surgical instrument comprises a stabilizer, said stabilizer being positionable on a beating heart.

26. A surgical access platform comprising a hub,
   first and second blade interconnected to said hub, said first and second blades being adapted to engage opposing incision edges of a chest incision, with adjustment of said hub causing relative lateral displacement between said first and said second blades, and
   a torsional member operably interconnected to said first blade and said hub, with adjustment of said torsional member causing generally vertical bi-directional displacement of said first blade relative to said second blade.

27. The surgical access platform of claim 26, further comprising a support pad interconnected to said first blade.

28. The surgical access platform of claim 27 wherein said support pad is adjustably interconnected to said first blade.

29. The surgical access platform of claim 26, further comprising a first support pad and a second support pad interconnected to said first and second blades respectively.

30. The surgical access platform of claim 26, wherein said hub further comprises an upper hub rotatably connected to a lower hub.

31. The surgical access platform of claim 26, wherein said hub further comprises a ratchet mechanism operably interconnecting a first hub member to a second hub member.

32. The surgical access platform of claim 26, wherein said hub further comprises a harmonic gear assembly operably interconnecting a first hub member to a second hub member.

33. The surgical access platform of claim 30, further comprising first and second spreader arms extending from said upper and lower hubs respectively.

34. The surgical access platform of claim 26, wherein said first blade further comprises an elongated vane.

35. The surgical access platform of claim 26, wherein said first blade further comprises a recessed throat.

36. The surgical access platform of claim 26, wherein the torsional member further comprises a first member operably connected to a second member.

37. The surgical access platform of claim 36, wherein said first member further comprises a reduction gear.

38. The surgical access platform of claim 36, wherein said first member further comprises a ratchet mechanism.

39. The surgical access platform of claim 26, further comprising a tissue retractor operably interconnected to said first blade.

40. The surgical access platform of claim 26, further comprising a blade arm extending from said first blade and operably connected to said torsional member.

41. The surgical access platform of claim 40, further comprising a tissue retractor pivotally connected to said blade arm and connected to said first blade.

42. A method of thoracic surgery comprising the steps of
   providing a surgical access platform, said platform comprising first and second blades adapted to engage opposing sides of a chest incision, a spreader member interconnected to said first and second blades, and a displacement member operably interconnected to said first blade and said spreader member, with adjustment of said displacement member causing generally vertical bi-directional displacement of said first blade relative to said second blade,
   positioning said first and second blades in a chest incision to engage opposing sides of the incision,
   spreading said first blade relative to said second blade in a generally lateral direction, and
   displacing said first blade relative to said second blade in a generally vertical direction to vertically offset opposing sides of the incision.

43. The method of thoracic surgery of claim 42, further comprising the steps of
   providing a support pad interconnected to said first blade,
   positioning said support pad on the chest adjacent the sternum, and
   depressing the sternum adjacent said support pad.

44. The method of thoracic surgery of claim 42, further comprising the steps of
   providing a second displacement member interconnected to said second blade and said spreader member, and
   displacing said second blade in a generally vertical direction opposite to the displacement of said first blade.

45. The method of thoracic surgery of claim 42, further comprising the steps of
   providing a stabilizer interconnected to said second blade, and
   positioning said stabilizer on a beating heart to stabilize said beating heart.

* * * * *

UNITED STATES PATENT AND TRADEMARK OFFICE
CERTIFICATE OF CORRECTION

PATENT NO. : 5,730,757
DATED : March 24, 1998
INVENTOR(S) : Federico J. Benetti et al.

It is certified that error appears in the above-identified patent and that said Letters Patent is hereby corrected as shown below:

On the title page, item [56],

Please insert the following Cited References:

U.S. Patent Document:

5,025,779        6/1991        Bugge

Column 1, line 43, please change "by pass" to -- bypass --.

Column 1, line 53, please change "IMA" to -- internal mammary artery (IMA) --.

Column 4, line 46, please change "platform," to -- platform --.

Column 4, line 57, after "bar" please insert -- for --.

Column 4, line 58, after "blade" please delete -- arm --.

Column 4, line 59, after "bar" please insert -- in FIG. 14 --.

Column 5, line 65, after "hub" please insert -- half --.

UNITED STATES PATENT AND TRADEMARK OFFICE
CERTIFICATE OF CORRECTION

PATENT NO. : 5,730,757
DATED : March 24, 1998
INVENTOR(S) : Federico J. Benetti et al.

It is certified that error appears in the above-identified patent and that said Letters Patent is hereby corrected as shown below:

Column 8, line 29, please change "IRA" to -- IMA --.

Column 11, lines 6, before "231" please insert -- blade --.

Column 11, line 31, please change "$A_i$" to -- $A_1$ --.

Column 11, line 39, after "used" please insert -- to --.

Column 13, line 15, please change "361 and 365" to -- 461 and 465 --.

Column 13, line 28, please change "driver" to --driven--.

Column 13, line 56, please change "blade" to --blades--.

Column 15, line 15, please change "blade" to --blades--.

Signed and Sealed this

Fifteenth Day of August, 2000

Attest:

Q. TODD DICKINSON

Attesting Officer

Director of Patents and Trademarks